United States Patent [19]
Vakharia et al.

[11] Patent Number: 5,871,744
[45] Date of Patent: Feb. 16, 1999

[54] METHOD FOR GENERATING BIRNAVIRUS FROM SYNTHETIC RNA TRANSCRIPTS

[75] Inventors: Vikram N. Vakharia, Bowie, Md.; Egbert Mundt, Rieurserorf, Germany

[73] Assignee: University of Maryland-Biotechnology Inst., College Park, Md.

[21] Appl. No.: 708,541

[22] Filed: Sep. 5, 1996

[51] Int. Cl.$^6$ .................. A61K 39/12; A61K 39/00; A61K 39/38

[52] U.S. Cl. .................. 424/205.1; 424/184.1; 424/186.1; 424/185.1; 424/204.1; 424/816; 424/826; 435/71.1; 435/235.1; 435/236; 435/237; 435/238; 435/239; 435/320.1; 536/23.72

[58] Field of Search .................. 424/184.1, 204.1, 424/816, 826, 186.1, 185.1, 205.1; 435/71.1, 235.1, 236–239, 320.1; 536/23.72

[56] References Cited

U.S. PATENT DOCUMENTS

| 4,530,831 | 7/1985 | Lutticken et al. | 424/89 |
| 5,192,539 | 3/1993 | VanDer Marel et al. | 424/89 |
| 5,310,678 | 5/1994 | Bingham et al. | |

FOREIGN PATENT DOCUMENTS

| 0352835 A1 | 1/1990 | European Pat. Off. | |
| WO86/07060 | 12/1986 | WIPO . | |
| WO91/05569 | 5/1991 | WIPO . | |
| 91/16925 | 11/1991 | WIPO | A61K 39/15 |
| WO91/16925 | 11/1991 | WIPO . | |
| WO93/03145 | 2/1993 | WIPO . | |
| WO94/06904 | 3/1994 | WIPO . | |

OTHER PUBLICATIONS

Egbert Mundt & Hermann Müller, Virology, *Complete Nucleotide Sequences of 5'–and 3'–Noncoding Regions of Both Genome Segments of Different Strains of Infectious Bursal Disease Virus,* (1995), pp. 10–18, vol. 209.

U. Spies & H. Müller, Journal of General Virology, *Demonstration of enxyme activities required for cap struture formation in infectious bursal disease virus, a member of the birnavirus group,* (1990), pp. 977–981, vol. 71.

S. Zou & E.G. Brown, Virology, *Identification of Sequence Elements Containing Signals for Replication and Encapsidation of the Reovirus M1 Genome Segment,* (1992), pp. 377–388, vol. 186.

Mario I. Gorziglia & Peter L. Collins, Proc. Natl. Acad. Sci. USA, *Intracellular amplification and expression of a synthetic analog of rotavirus genomic RNA bearing a foreign marker gene: Mapping cis–acting nucleotides in the 3'–noncoding region,* Jul. 1992, pp. 5784–5788, vol. 89.

Jean–Christophe Boyer & Anne–Lise Haenni, Virology, *Infectious Transcripts and cDNA Clones of RNA Viruses,* (1994), pp. 415–426, vol. 198.

Sylvie Van Der Were, Jonathan Bradley, Eckard Wimmer, F. William Studier, & John J. Dunn, Proc. Natl, Acad. Sci. USA, *Synthesis of infectious poliovirus RNA by purified T7 RNA polymerase,* Apr. 1986, pp. 2330–2334, vol. 83.

Wilem Luytjes, Mark Krystal, Masasyoshl Enami, Jeffrey D. Parvin, & Peter Palese, Cell, *Amplification, Expression and Packing of a Foreign Gene: by Influenza Virus,* Dec. 22, 1989, pp. 1107–1113, vol. 59.

Matthias J. Schnell, Teshome Mebatsion & Karl–Klaus Conzelmann, The Embo Journal, *Infectious rabies viruses from cloned cDNA,* (1994), pp. 4195–4203. vol. 13.

Michael R. Roner, Lisa A. Sutphin, & Wolfgang K. Joklik, Virology, *Reovirus RNA Is Infectious,* (1990), pp. 845–852, vol. 179.

Vikram N. Vakharia, Junkun He, Basheer Ahamed, David B. Synder, Virus Research, *Molecular basis of antigenic variation in infectious bursal disease virus,* (1994), pp. 265–273, vol. 31.

H. Müller, H. Lange & H. Becht, Virus Research, *Formation, characterization and interfering capacity of a small plaque mutant and of incomplete virus particles of infectious bursal disease virus,* (1986), pp. 297–309, vol. 4.

Baoshan Chen, Gil H. Choi, & Donald L. Nuss, Science, *Attenuation of Fungal Virulence by Synthetic Infectious Hypovirus Transcripts,* 17 Jun. 1994, pp. 1762–1764, vol. 264.

Peter Dobos, Virology, *Protein–Primed RNA Synthesis in Vitro by the Virion–Associated RNA Polymerase Of Infectious Pancreatic Necrosis Virus,* (1995), pp. 19–25, vol. 208.

John T. Patton, Virus Research, *Synthesis of Simian Rotavirus SA11 Double–Stranded RNA in A Cell–Free System,* (1986/87), pp. 217–233, vol. 6.

Michael Schonberg, Samuel C. Silverstein, Daniel H. Levin, & George Acs, Proc. Natl. Acad. Sci., *Asynchronous Synthesis of the Complementary Strands of the Reovirus Genome,* Feb. 1971, pp. 505–508, vol. 68, No. 2.

(List continued on next page.)

*Primary Examiner*—Michael P. Woodward
*Assistant Examiner*—Datquan Lee
*Attorney, Agent, or Firm*—Nikaido, Marmelstein Murray & Oram LLP

[57] ABSTRACT

A system for the generation of live Birnavirus such as infectious bursal disease virus (IBDV), a segmented double-stranded (ds)RNA virus of the Birnavirdae family, using synthetic transcripts derived from cloned DNA has been developed. Independent full-length cDNA clones were constructed which contained the entire coding and non-coding regions of RNA segments A and B of IBDV, respectively. Synthetic RNAs of both segments were produced by in vitro transcription of linearized plasmids with T7 RNA polymerase. Transfection of Vero cells with combined plus-sense transcripts of both segments generated infectious virus as early as 36 hours post-transfection. The development of a reverse genetics system for dsRNA viruses will greatly facilitate studies of the regulation of viral gene expression pathogenesis, and design of a new generation of live and inactivated vaccines.

14 Claims, 12 Drawing Sheets

OTHER PUBLICATIONS

Dayue Chen, Carl Q.–Y. Zeng, Melissa, J. Wentz, Mario Gorziglia, Mary K. Estes, & Robert F. Ramig., Journal of Virology, *Template–Dependent, In Vitro Replication of Rotavirus RNA,* (Nov. 1994, pp. 7030–7039, vol. 68, No. 11.

Bayliss et al."A comparison of the sequences of segment A of four infectious bursal disease virus strains and identification of a variable region VP2". Journal of General Virology. vol. 71, pp. 1303–1312, 1990.

Mundt et al. "Identification of a novel viral protein in infectious bursal disease virus infected cells". Journal of General Virology. vol. 76, pp. 437–443, 1995.

Mundt et al. "Complete Nucleotide Sequences of 5' and 3' Noncoding Regions of Both Genome Segments of Different Strains of Infectious Bursal Disease Virus". Virology. vol. 209, pp. 10–18, 1995.

Spies et al. "Nucleotide sequence of infectious bursal disease virus genome segment A delineates two major open reading frame". Nucleic Acids Research. vol. 17, No. 19, p. 7982, 1989.

Morgan et al. "Sequence of the Small Double Stranded RNA Genomic Segment of Infectious Bursal Disease Virus and Its Deduced 90kDa Product". Virology. vol. 163, pp. 240–242, 1988.

segment A of
strain 23/82

```
          SEQ ID No. 3
CGGCGAATTCATGCA TAGGGGACCCGCGAACGGATC
GCCGCTTAAGT ACGTATCCCCTGGGCGCTTGCCTAG
EcoR I    Nsi I
``` pUC18FLA23

── VP'3-VP4-VP2 ──[VP5]

Transcription →

```
         SEQ ID No. 4
 GTCAGACCGATCGTATCCTATAGTGAGTCGTATTAGAATTCTCT
CAGTCTGGCTAGCATAGGATATCACTCAGCATAATCTTAAGAGA
                                      EcoR I
```

Fig.1B segment B of
strain P2 pUC18FLBP2

SEQ ID No. 5
TTGCATGCTGCA GGGGGCCCCCGCAGGCGAAG
AACGTACGG ACGTCCCCGGGGGCGTCCGCTTC
           |Pst I

VP1

SEQ ID No. 6
TCGTATCCTATAGTGAGTCGTATTAGAATTC
AGCATAGGATATCACTCAGCATAATCTTAAG
                                EcoR I

Transcription →

Fig.1C

Segment A

```
                530        540        550        560        570        580
23-82A         GGAAGCCTGAGTGAGTTGACTGACTACAGCTACAACGGGCTGATGTCAGCCACTGCGAAC
SEQ ID No. 7
23A/P2B        ...........................................................
SEQ ID No. 8   GGAAGCCTGAGTGAGTTGACTGACTACAGCTACAACGGGCTGATGTCAGCCACTGCGAAC
P2A            ...........................................................
SEQ ID No. 9   GGAAGCCTGAGTGAACTGAACTGACAGATGTTAGCTACAATGGGTTGATGTCTGCAACAGCCAAC
                530        540        550        560        570        580

590        600        610        620        630        640
23-82A         ATCAACGACAAGATCGGGAACGTTCTAGTTGGAGAAGGGGTGACTGTTCTCAGTCTACCG
SEQ ID No. 7
23A/P2B        ...........................................................
SEQ ID No. 8   ATCAACGACAAGATCGGGAACGTTCTAGTTGGAGAAGGGGTGACTGTTCTCAGTCTACCG
P2A            ...........................................................
SEQ ID No. 9   ATCAACGACAAAATTGGGAACGTCCTAGTAGGGGAAGGGGTCACCGTCCTCAGCTTACCC
                590        600        610        620        630        640
```

Fig.3A

Segment B

```
                    130        140        150        160        170        180
23-82B              TTTTCAATAGTCCACAGGGCGCGAACGAAGAAGATCTCAGCAGCGTTCGGCATAAAGCCTACTG
SEQ ID No. 10
23A/P2B             TTTTCAACAGTCCACAGGGCGCGAAGCACGATCTCAGCAGCGTTCGGCATAAAGCCTACTG
SEQ ID No. 11
P2B                 TTTTCAACAGTCCACAGGGCGCGAAGCGCGAAGCACGATCTCAGCAGCGTTCGGCATAAAGCCTACTG
SEQ ID No. 12
                    130        140        150        160        170        180

190        200        210        220        230        240
23-82B              CTGGACAAGAGACGTGGAAGAACTCTTGATCCCCAAAGTCTGGGTGCCACCTGAGGATCCGC
SEQ ID No. 10
23A/P2B             CTGGACAAGAGACGTGGAAGAACTCTTGATCCCTAAAGTTTGGGTGCCACCTGAGGATCCGC
SEQ ID No. 11
P2B                 CTGGACAAGAGACGTGGAAGAACTCTTGATCCCTAAAGTTTGGGTGCCACCTGAGGATCCGC
SEQ ID No. 12
                    190        200        210        220        230        240
```

```
                  10          20          30          40          50          60          70
    1  GGATACGATCGGTCTGACCCCGGGGAGTCACCCGGGACAGGCCATCACTGCCTTGTTCCTGGTTGGAA
   71  CTCCTCTTTCTGCTGTACTACTGCCAACAGATTGTTCCGTTCATGCGGTGAGTAGAGATCAGACAAACGATCGCAGCGATGACAAACC
  141  TGATGGATCACACCCAACAGATTGTTCCGTTCATACGGAGCCTTCTGATGCCAACGACCGGACCGGCGTC
  211  CATTCCGACGACGACACCCTGGAGAAGCACACACTCAGGTCCGACTTACAACTTGACTGTAGGG
  281  GATACAGGGTCAGGACTAATTGTCTTTTCCCTGGATTCCTGGTTCAGTTGAGGTGCTCACTACACAC
  351  TGCAGAGCAGTGGGAACTACCAATTCGACCAGATGCTCCTGACAGCGCAGAACCTGCCTGCCAGTACAA
  421  CTACTGCAGGCTAGTGAGCAGGAGTCTAACGGTCAAGCCGTAACCGTCAAGGAAGCCTCCCTGGTGGCGTTTATGCACTA
  491  AACGGAACCATAAACGCAGTGACCTTCCACGGAAGCCTGAGTGAGTTGACTGAGTTGAGAGTTGACTGTTCT
  561  TGATGTCAGCCACTGCGAACATCAACGACAAGATCGGTGAGAAGATCGGTTCTAGTTGAGAAGGGGTGACTGTTCT
  631  CAGTCTACCAGCTTCATATGTGAGACTTCGGTGACCCATCCCGCAGCAGGACTCGAC
  701  CCGAAGTTGATGGCCACGTGCGACAGTAGTGACAGAGACCCAGAGTCTACACCAGAGTCTGCAGATCTGCAGATGCTCT
  771  ACCAATTCTGTCACAACTCATCCCGAGTGCGTGAAGACGTAACAACATTGAAGTGGACGTC
  841  CACCAGCTTCAGGTTGGTGGTTTGACGGGACAGAGACGTAGCAGTCAAGGCAGTTGCAACAGACTTTGGGCTGA
  911  ACCATTCACTTCATTGGGTTTGACGGGACAGAGACGTAGCAGTCAAGGCAGTTGCAACAGATCACCCAGCCATCAC
  981  CAACTGGGACAAAACCTTGTGCCATTCAACCTGGTGGTCCCAACAAATGAGATCACCCAGCCATCAC
 1051  TTCCATGAAACTAGAGGTTGTGACCTACAAGATTGGGCGCACCGCTGGTGTGACCCAATATCATGGACAGTG
 1121  AGTGGTACACTAGCTGTGACGGTGCACGGAGGCAACTACCCTGGGGCTCTCCGTCCTGTCACCCTGGTGG
 1191  CCTATGAACGAGTGGCTGCAGGATCTGTTGTCACAGAGTATGGCCGCTTTGACCCCGGAGCAACTTCGAGCTAATCCCCAA
 1261  CCCTGAGCTTGCAAAGATGAGAGAACCTAGTTACAGAGTATGGCCGCTTTGACCCCGGAGCAATGAACTACACCAAA
 1331  CTAATACTGAGTGAGTAGAGATCGTCTAGGCATCAAGACAGTCTGGCCCACCAGGGAGTACACCGATTGA
 1401  GGGAGTACTTCATGGCCATTCGCAGATCTCAACTCACCCCTAAAGATTGCAGGAGCATTTGGCTTTAAGGA
 1471  CATAATCCGAGCCAATGCAGGAGAAGGTGTAGAGCTGCCTCCAGTGTATCCCAGTGGTTGCCACCTCTTCCCTGCACCCTA
 1541  GCACATGGCACATCGGAGGAGAAAAGCTAGAGCTGCCTCCAGGACGAATAAGGCAGTAACTCTGCAGCCTCAGGGACAGCTC
 1611  GAGCCGCGTCAGGAGTAGTCGCCAACATGTTCCAGGTGCCCCAGAATCCCATTGTTGATGCCATTCGGCATCCCCA
 1681  GTGCGAGGTAGTGCACACAGAAACCTCGACTGCTATGGGAGGAGCCACTCTTTCCCTGTGTCA
 1751  GGAATCCTGCGTGGGCGCACACAAACCTCGACTGCTATGGGAGGAGCCACTCTTTCCCTGTGTCA
```

```
1821  TTACGACACTCGAGGATGAGCTGACCCCCAAGGCACTGAACAGCAAAATGTTTGCTGTCATTGAAGGTGT
1891  GCGAGAGGACCTCCAGCCTCCATCCCCAACGGGATCCTTCATTCGAACTCTCTCTGGCCATAGAGTCTAT
1961  GGCTATGCCCCAGACGGAGTACTGCCTCTGGAGACCGGAGAGACTACACCGTTGTCCCAATTGATGATG
2031  TGTGGGACGATAGCATAATGCTGTCGCAGGACCCCATACCTCCAATCATAGGGAACAGCGGCAACCTAGC
2101  CATAGCATACATGGATGTCTTCAGGCCCAAGGTCCCCATCGGCTATGACACAGCCCACCACTTGGCATGCC
2171  CGCGGTGAGATCGAGAGTGTTACGTTCCGVAGCACCAAACTCGCCACAGCCCACGACTTGGCATGAAGT
2241  TAGCTGGTCCTGGAGCCTATGACATTAATACAGGACCTAACTGGGCAACGTTCGTCAAACGTTTCCCTCA
2311  CAATCCCCGAGAGACTGGGACAGGTTGCCCTAACCTTCCTTATCTCCACCAACAGCAGGACGTCAG
2381  TTCCATCTAGCCCTGGCTGCCTCCGAGTTCAAAGAGACCCCAGAACTCGAAGACGCTGTGCGCAATGG
2451  ATGCCGCTGCAAATGCCGACCCATTGTTCCGCTCAGCTCTTCATGTGGTTGGAAGAAAAACTTCCTAGCA
2521  GATTGTGACCGACATGGCTAACTTCGCCCCTCAGCGACCAAACGCGCATAGGATGAAAAACGCGCTAGCA
2591  AACGCACCCAGGCTGGAAGCAAGTCCACAGAGGAAAAAGACACACGGATCTCCAAGAGATGGAAACAATGGG
2661  GAGGCCCCACACCAGAGGAAAAAGACACACGGATCTCCAAGAGATGGAAACAATGGG
2731  CATCTACTTCGCGAGAACACGGAATGGGTGGCTCTCAACGGGCACCGAGGCCCAAGCCCAACTCAAG
2801  TACTGGCAAAACACAAGAGAAATACCAGAGACCCAATGAGGACTACCAGATCTACGGGCTCCAGGACAGGCTGA
2871  GCCGGTTGGCGTCAGAAGAACAGATCCTACGGGCAGCCACGTCGATCTCGAAATCAACCATGGGCGTGGTCCAAACCAG
2941  ACCACCCCAGGCCTTCATAGACGAGGTCGCCAGGGTCTACTGCGATGGAGATGAAGCATCGCAATCCCAGGCGGCTCCACCAA
3011  GAGCAGATGAAGGACCTGCTCCTGACTGCCATCACAGAGACCCCCTGGACGGCTGGACCGCTGATCAGGACGGT
3081  AGCCAAAGCCAAAACCCAATGCTCCATCACAGAGACCCCCCTGGACGGCTGGACCGCTGATCAGGACGGT
3151  CTCCGACGAGGACTTGGAGTGAGGCTCCTGGGAGTCTCCGACACTACCCCGCCAGGTGTGGACACCAAT
3221  TCGGCCCTTCTACCATCCCAAATTGGATCCGTTCGCGGGTCCCCT
```

Total number of bases is: 3264.
DNA sequence composition: 834 A; 942 C; 853 G; 635 T;

Sequence name: 23-82A (SEQ ID NOS: 31 and 33)

```
     10         20         30         40         50         60         70
1    GGATACGATCGGTCTGACCCCGGG GGAGTCACCCGGGACAGGCCGTCAAGGCCTTGTTCCAGGATGGGA
71   CTCCTCCTTCTACAACGCTATCATTGATGGTTAGTAGAGATCAGACAAACGATCGCAGCGATGACAAACC
141  TGCAAGATCAAACCCAACAGATTGTTCCGTTCATACGGAGCCTTCTGATGCCAACAACCGACCGGCGTC
211  CATTCCGACGACACCCTGGAGAAGCACACTCTCAGGTCAGAGACCTCGACCTCAATTGTGGCTCACTACACAC
281  GACACAGGGTCAGGGCTAATTGTCTTTTCCCTGGATTCCCTGACTGCTCTGACTGCCCAGAACCTACCGGCCAGTTACAA
351  TGCAGGGCAATGGGAACTACAAGTTCGATCAGATGCTCTCACAGTGAGGTCAAGCACACTTCCTGGTGGCGTTTATGCACTA
421  CTACTGCAGGCTAGTGAGTCGGAGTCTCACAGTCTCACAGTGAGGTCAAGCACACTTCCTGGTGGCGTTTATGCACTA
491  AACGGCACCATAAACGCCGTGACCTTCCAAGGAAGCCTGAGTGAACTGAACGTGAACTGAGATGTTAGCTACAATGGGT
561  TGATGTCTGCAACAGCCAACATCAAGACACAAATTGGGAACGTCCTAGTAGGGAAGGGGTCACCGTCCT
631  CAGCTTACCCACACATCATATGATCTTGGGTATGTGAGGCTTGGTGACCCATTCCCGCAATAGGGCTTGAC
701  CCAAAAATGTAGCCACATGGCCACAGTGACAGCAGTCTACACAGAGTCTACACCATAACTGCAGCCGATGATT
771  ACCAATTCTCATCACAGTACCAACCAGTGGGTAACAATCACACACTGTTCTCAGCCAACATTGATGCCAT
841  CACAAGCCTCAGCTGCGTTGGGGAGAGCTCGTGTTTCAAACAACAAGCGTCATCACCCCTTGTACTGGGCGCCACC
911  ATCTACCTCATAGGCTTTGATGGGACAACGGTAATCTTGTGATTCCAACAAACGAGATAACCCAGCAATCACATC
981  CCGGCACCGACAACCTTATGCCATTCAATCTTGTGATTCCAACAAACGAGATAACCCAGCAATCACATC
1051 CATCAAACTGGAGATAGTGACCTCCAAAAGTGGTCAGGCAGGGATCAGATGTCATGGTCGGCAAGA
1121 GGGAGCCTAGCAGTGACGATCCATGGCAACTATCCGGTCGCTGGGGTGAGCAACTTCGAGCTGATCCCAAATCC
1191 ACGAAAGAGTGGCAACAGGAACCTGGTTACAGAATACGGCCGATTTGACCCAGGAGCCATGAACTACACTGACTTTCGTG
1261 TGAACTAGCAAGAGTGGCAACAGGAACCTGGTTACAGAATACGGCCGATTTGACCCAGGAGCCATGAACTACACTGACTTTCGTG
1331 ATACTGAGTGCGAGAGGACCGTCTTGGCATCAAGACCGTCTGCCAACAAGGAGTACACTGACTTTCGTG
1401 AATACTTCATGGAGGTGGCCGAACCTCAACTCTCCCCTGAAGATTGCAGGAGCATTCGGCTTCAAAGACAT
1471 AATCCGGCCATAAGGAGGATAGCTGTGCCGGTGGTCTCCACATTGTTCCACCTGCCGCTCCCCTAGCC
1541 CATGCAATTGGGGAAGGTGTAGACTACCTGCCTCAGGCGGATGAGGCACAGGCTGCTTCAGGAACTGCTCGAG
1611 CCCGTCAGGAGTCGCCTCAGGCCGCATAAGGCCGCATAAGAATCCCGTAGTAGTCGACGGGATTCTTGCCCGA
1681 CGAGGTAGTCGCGAATCTATTCCAGGTGCCCAGAATCCCGTAGTAGTCGACGGGATTCTTGCTTCACCTGGG
1751 GTACTCCGGGTGCAACCTCGACTGCGGTGTTAAGAGAGGGTGCCACGTCCTATTCCCTGGTTATTA
```

```
1821  CGACAGTGGAAGACGCCATGACACCCAAAGCATTGAACAGCAAAATGTTTGCTGTCATTGAAGGCGTGCG
1891  AGAAGACCTCCAACCTCCATCTCAAAGAGGATCCTTCATACGAACTCTCTGGACACAGAGTCTATGGA
1961  TATGCTCCAGATGGGTACTTCCACTGGAGAGACTCCCATACCTCCTATTGTGTGGAAACAGTGGAAATCTAGCGATGTCT
2031  GGGACGACAGCAGCATTATGCTGTCTCCAAAGATCCCATACCTCCTATTGTGTGGAAACAGTGGAAATCTAGCCAT
2101  AGCTTACATGGATGTGTTTCGACCCAAAGTCCCAATCCATGTGGCTATGACGGGAGCCCTCAATGCTTGT
2171  GGCGAGATTGAGAAAGTAAGCTTTAGAAGCACCAAGCTCGCCACTGCACACCGACTTGGCCTTAGGTTGG
2241  CTGGTCCCGGAGCATTCGATGTAAACACCGGGCCCAACTGGCAACGTTCATCAAACGTTTCCCTCACAA
2311  TCCACGCCACTGGGACAGGCTCCCCTACCTCAACCTACCATACCTTCCACCCAATGCAGGACGCCAGTAC
2381  CACCTTGCCATGGCTGCATCAGAGTTCAAAGAGACCCCCGAACTCGAGAGTGCCGTCAGAGCAATGGAAG
2451  CAGCAGCCAACGTGGACCACTGGACCCACTATTCCACTCGCACTCAGTGTGTTCATGTGGCTGGAAGAGAATGGGAT
2521  TGTGACTGACATGGCCAACTTCGCACTCAGCGACCCGAACGCCCATCGGATGCAGGCTACGGGACAGGCTACGGAGTGGAGGCTCGGG
2591  GCACCACAAGCAGGAAGCAGCAAGTCGCAAAGGGACAAGACACAGAGGGAAAAAGAGACATCTCAAAGAAGATGGAGACCATGGGCAT
2661  GCCCCACACCAGAGGAAGAACCAGAATGGGTAGCACTCAATGGCACCGAGGGCAAGCCCCGGCCAGCTAAAGTAC
2731  CTACTTTGCAAGAACACCGAGAAGAACAACAAATCCTAAGGGCAGCTACGTCGATCTCGATCTCGATCTACGGGGCGCCAAACCAAGAA
2801  TGGCAGAACACAGAGAAGAACAACAAATCCTAAGGGCAGCTACGTCGATCTCGATCTACGGGGCCAAACCAAGAA
2871  GGTTGGCATCAGAAGACGAAGTTGCCAAGTCTATGAAATCAACCATGCAATCGCAGCATCCCAGGCGCTCTACCAAAGC
2941  ACCCCAAGCTTTCATAGACGAAGTTGCCAAGTCTATGAAATCAACCATGCAATCGCAGCATCCCAGGCGCTCTACCAAAGC
3011  CAGATGAAAGATCTGCTCTTGACTGCGATGGAGATGAAGCATGAGAGACCCCCTGGTCGGCTGGCTGGATCAGGACCGTCTC
3081  CCAAGCCAAAACCCAAATGCTCCAAACAGAGAGAGACCCCCTGGTCGGCTGGCTGGATCAGGACCGTCTC
3151  TGATGAGGACCTTGAGTGAGGCTCCTGGAGTCTCCCGACACCACCCGGCAGGTGTGGACACCAATTCG
3221  GCCTTACAACATCCCAAATTGGATCCGTTCGCGGGTCCCCT
```

Total number of bases is: 3261.

DNA sequence composition: 873 A; 909 C; 847 G; 632 T; 0 OTHER;

Sequence name: D78F (SEQ ID NOS: 27 and 29)

```
              10         20         30         40         50         60         70
    1  GGATACGATGGGTCTGACCCTCTGGGAGTCACGAATTAACGTGGCTACTAGGGGCGATACCCGCCGCTGG
   71  CCGCCACGTTAGTGGCTCTCTCTTCTTGATGATTCTGCCACCATGAGTTGACATTTCAACAGTCCACAGGC
  141  GCGAAGCACGATCTCAGCAGCGTTCGGCATAAAGCCTACTGCTGGACAAGACGTGGAAGAACTCTTGATC
  211  CCTAAAGTTTGGGTGCCAACCTGAGGATCCGCTTGCCCAGCCCTAGTCGACTGGCAAAGTTCCTCAGAGAGA
  281  ACGGCTACAAAGTTTTGCAGCCACGGTCTCTGCCCGAGAATGAGGAGTATGAGACCGACCAAATACTCCC
  351  AGACTTAGCATGGATGCGACAGATAGAAGGGGCTGTTTTAAAACCCACTCTATCTCTCCCTATTGGAGAT
  421  CAGGAGTACTTCCCAAAGTACTACCCAACACATCGCCCTAGCAAGGAAGCCAATGCGTACCCGCCAG
  491  ACATCGCACTACTCAAGCAGATGATTACCTTGCTGTTTCTCCAGGTTCCAGAGAGGCCAACGAGGGCCTAAAGGA
  561  TGAAGTAACCCTCTTGACCCAAGACATAAGGGACAAGGCCTATGGAAGTGGGACCTACATGGGACAAGCA
  631  AATCGACTTGTGTGGCCATGAAGGAGGTCGCCACTGGAAGAAACCCAAACAAGGATCCTCTAAAGCTTGGGT
  701  ACACTTTTGAGAGCATCGCGCAGCTACTTGACATCACACTACCGGTAGGCCCACCCGGTGAGGATGACAA
  771  GCCCTGGG TGCCACTCACAAGAGTGCCGTCACGGATGTTGGTGCTGACGGGAGACGTAGATGGCGACTTT
  841  GAGGTTGA AGATTACCTTCCCAAATCAACCTCAAGTCATCATCAACCAGTTCTCAGAGAGCTATCAACACTGTTGAA
  911  AAGG AGAGACAATTGGCGAGATGATAGCTATCTCAAACAAGAAGAAGCTACTCAGCATGTTAAGTGACTATTGGTACTTA
  981  GCAAGGTG CAGGGACAAAGGGGTCAAACAAGGCTGAAAGGTACGACACAAAGTACTACCTGGCCCGTGATGTCCAACAGCCC
 1051  TCAT GCGGGCTTTTGTTTCCAAAGCTACACACCTCATGATCTCTATGACTCACCTGGCCCGTTCAACCCGTTCAGAGGAGGGTTGAAC
 1121  TATGGTCAGCTCCATCCCAAACACACACCTCATGATCTCTATGACTCACCTGGCCCGTGATGTCCAACAGCCC
 1191  AAAT AACGTGTTGAACATTGAAGGGATATTGCCCCGGAAGACCTCTTGTATATGCGGACAACATATACATTG
 1261  AGGA TCGTCGAGTGGATATTGCCCCGGAAGACCTCTTGTATATGCGGACAACATATACATTG
 1331  TCCA CTCAAACACGTGGTACTCAATTGACCTAGAGAAGGGTGAGGCAAACTGCACTCGCCAACACACATGCA
 1401  AGCCGCAATGTACTAGTACTACTCAAGCAGACCCAGAGACAGCCCAGAGACAGCAGGAGGAGTTCAATCAATGAACCTGCAAA
 1471  GCCACCTTTGCCATGAACATTGCCCCTGCTCTCAGTGGTCATCGTGCCTGATAATGAACCTGCAAA
 1541  TTAAGACCTATGGTCAAGGCAGCAGGGAATGCAGCCACGTTCATCAACAACACCTCTTGAGCACACTAGT
 1611  GCTTGACCAGTGGAACCTGATGAGACCTGATGAGACAGCCCAGAGACAGGAGAGTTCAAATCAATTGAGGACAAG
 1681  CTAGGTATCAACTTTAAGATTGAGAGGTCCATTGATGATATCAGGGACGTGAGACAGCTTGTCCTCC
 1751  TTGCACAACCAGGGTACCTGAGTGGTGGGGGGTTGAACCAGAGAACAATCCAGCCCAACTGTTGAGCTTGACCT
```

```
1821  ACTAGGGTGGTCAGCTACATACAGCAAAGATCTCGGGATCTATGTGCCGGTGCTTGACAAGGAACGCCTA
1891  TTTGTTCTGCTGCGTATCCCAAGGGAGTAGAGAACAAGAGTCTCAAGTCCAAGTCGGGATCGGAGCAGG
1961  CATACAAGGTAGTCAGGTATGAGGCGTTGAGGTTGGTAGGTGGTTGGAACTACCCACTCCTGAACAAAGC
2031  CTGCAAGAATAACGCAGGCGCGCCGCTCGGCGGCATCTGGAGGCCAAGGGGTTCCCACTCGACGAGTTCCTA
2101  GCCGAGTGGTCTGAGCTGTCAGAGTTCGGTGAGGCCTTCGAAGGCTTCAATATCAAGCTGACCGTAACAT
2171  CTGAGAGCCTAGCCGAACTGAACAAGCCAGTACCCCCCAAATGTCAACAGACCAGTCAACAC
2241  TGGGGACTCAAGGCAGTCAGCAAGACGTCAGCAACGCCCTCAAGACCGGTCGGTACAGGAACGAAGCCGGACTGAGTGGT
2311  CTCGTCCTTCTAGCCACAGCCAGAAGCCGTCTGCAAGATGCAGTTAAGGCCAAGGCAGAAGCCGAGAAAC
2381  TCCACAAGTCCAAGCCGACTTCGCCAGCAAGGTCGCCCACTCAGCACTCGTGGAAACAAGCGACGCCCTTGAAGCA
2451  GGAGAAAGCCGACATCGCCAGCAAGGTCGCCCACTCAGCACTCGTGGAAACAAGCGACGCCCTTGAAGCA
2521  GTTCAGTCGACTTCCGTGTACACCCCCAAGAGAGCCACGGTTCCAAGAACGCCGCTCTTCTCGGAGCAGGAACGAG
2591  TTGTTGGGCTCCACCTGCCCGCCAAGAGAGCCACGGTTCCAAGAACGCCGCTCTTCTCGGAGCAGGAACGAG
2661  CAGACCAATGGGGATGGAGGCCCCAACAGGTCCAAGAACGCCGTGAAAATGGCCAAACGGGCGGCAACGC
2731  CAAAAGGAGAGCCGCTAACAGCCATGATGGGAACCACTCAAGAGAGGACACTAATCCCAGACCCCGTAT
2801  CCCCGGCCCTTCGCCTGCGGGGGCCCCC
```

Total number of bases is: 2827.
DNA sequence composition: 796 A; 770 C; 724 G; 537 T; 0 OTHER;

Sequence name: P2B (SEQ ID No: 25)

Fig.6B

METHOD FOR GENERATING BIRNAVIRUS FROM SYNTHETIC RNA TRANSCRIPTS

BACKGROUND OF THE INVENTION

Infectious bursal disease virus (IBDV), a member of the Birnaviridae family, is the causative agent of a highly immunosuppressive disease in young chickens (Kibenge, F. S. B., et al., *J. Gen. Virol.*, 69, 1757–1775 (1988)). Infectious bursal disease (IBD) or Gumboro disease is characterized by the destruction of lymphoid follicles in the bursa of Fabricius. In a fully susceptible chicken flock of 3–6 weeks of age the clinical disease causes severe immunosuppression, and is responsible for losses due to impaired growth, decreased feed efficiency, and death. Susceptible chickens less than 3 weeks old do not exhibit outward clinical signs of the disease but have a marked infection characterized by gross lesions of the bursa.

The virus associated with the symptoms of the disease is called infectious bursal disease virus (IBDV). IBDV is a pathogen of major economic importance to the nation and world's poultry industries. It causes severe immunodeficiency in young chickens by destruction of precursors of antibody-production B cells in the bursa of Fabricius. Immunosuppression causes increased susceptibility to other diseases, and interferes with effective vaccination against Newcastle disease, Marek's disease and infectious bronchitis disease viruses.

There are two known serotypes of IBDV. Serotype I viruses are pathogenic to chickens whereas serotype II viruses infect chickens and turkeys. The infection of turkeys is presently of unknown clinical significance.

IBDV belongs to a group of viruses called Birnaviridae which includes other bisegmented RNA viruses such as infectious pancreatic necrosis virus (fish), tellina virus and oyster virus (bivalve mollusks) and drosophila X virus (fruit fly). These viruses all contain high molecular weight (MW) double-stranded RNA genomes.

The capsid of the IBDV virion consists of several structural proteins. As many as nine structural proteins have been reported but there is evidence that some of these may have a precursor-product relationship (Kibenge, F. S. B., et al., *J. Gen. Virol.*, 69, 1757–1775 (1988)). The designation and molecular weights of the viral proteins (VP) are as shown below.

TABLE 2

| Viral Protein | Molecular Weight |
|---|---|
| VP1 | 90 kDa |
| VP2 | 41 kDa |
| VP3 | 32 kDa |
| VP4 | 28 kDa |
| VP5 | 17 kDa |

Two segments of double-stranded RNA were identified in the genome of IBDV. The IBDV genome consists of two segments of double-stranded (ds)RNA that vary between 2827 (segment B) to 3261 (segment A) nucleotide base pairs (Mundt, E. et al., *Virology*, 209, 10–18 (1995)). The larger segment A encodes a polyprotein which is cleaved by autoproteolysis to form mature viral proteins VP2, VP3 and VP4 (Hudson, P. J. et al., *Nucleic Acids Res.*, 14, 5001–5012 (1986)). VP2 and VP3 are the major structural proteins of the virion. VP2 is the major host-protective immunogen of IBDV, and contains the antigenic regions responsible for the induction of neutralizing antibodies (Azad, et al., *Virology*, 161, 145–152 (1987)). A second open reading frame (ORF), preceding and partially overlapping the polyprotein gene, encodes a protein (VP5) of unknown function that is present in IBDV-infected cells (Mundt, E., et al., *J. Gen. Virol.*, 76, 437–443, (1995)). The smaller segment B encodes VP1, a 90-kDa multifunctional protein with polymerase and capping enzyme activities (Spies, U., et al., *Virus Res.*, 8, 127–140 (1987); Spies, U., et al., *J. Gen. Virol.*, 71, 977–981 (1990)).

It has been demonstrated that the VP2 protein is the major host protective immunogen of IBDV, and that it contains the antigenic region responsible for the induction of neutralizing antibodies. The region containing the neutralization site has been shown to be highly conformation-dependent. The VP3 protein has been considered to be a group-specific antigen because it is recognized by monoclonal antibodies directed against it from strains of both serotype I and II viruses. The VP4 protein appears to be a virus-coded protease that is involved in the processing of a precursor polyprotein of the VP2, VP3 and VP4 proteins.

Although the nucleotide sequences for genome segments A and B of various IBDV strains have been published, it was only recently that the complete 5'- and 3'-noncoding sequences of both segments were determined. The 5'-noncoding region of IBDV segments A and B contain a consensus sequence of 32 nucleotides, whereas the 3'-noncoding terminal sequences of both segments are unrelated, but conserved among IBDV strains of the same serotype (Mundt, E. et al., *Virology*, 209, 10–18 (1995)). These terminii might contain sequences important in packaging and in the regulation of IBDV gene expression, as demonstrated for other dsRNA containing viruses such as mammalian and plant reoviruses, and rotaviruses (Anzola, et al., *Proc. Natl. Acad. Sci. USA*, 84, 8301–8305 (1987); Zou, S., et al., *Virology*, 186, 377–388 (1992); Gorziglia, M. I., et al., *Proc. Natl. Acad. Sci. USA*, 89, 5784–5788 (1992)).

In recent years, a number of infectious animal RNA viruses have been generated from cloned cDNA using transcripts produced by DNA-dependent RNA polymerase (Boyer, J. C., et al., *Virology*, 198, 415–426 (1994)). For example poliovirus, a plus-stranded RNA virus; influenza virus, a segmented negative-stranded RNA virus; rabies virus, a non-segmented negative-stranded RNA virus; all were recovered from cloned cDNAs of their respective genomes (van der Werf, S., et al., *Proc. Natl. Acad. Sci. USA*, 83, 2330–2334 (1986); Enami, M., et al., *Proc. Natl. Acad. Sci. USA*, 87, 3802–3805 (1990); Schnell, M. J., et al., *EMBO J.*, 13, 4195–4205 (1994)). For reovirus, it was shown that transfection of cells with a combination of ssRNA, dsRNA and in vitro translated reovirus products generated infectious reovirus when complemented with a helper virus from a different serotype (Roner, M. R., et al., *Virology*, 179, 845–852 (1990)). However, to date, there has been no report of a recovered infectious virus of segmented dsRNA genome from synthetic RNAs only.

SUMMARY OF THE INVENTION

This invention relates to the infectious bursal disease virus (IBDV) that is associated with Gumboro disease of young chickens. More particularly, this invention relates to a system for the generation of infectious bursal disease virus (IBDV) using synthetic transcripts derived from cloned cDNA. The present invention will facilitate studies of the regulation of viral gene expression, pathogenesis and design of a new generation of live and inactivated vaccines.

DETAILED DESCRIPTION OF THE INVENTION

In an effort to develop a reverse genetics system for IBDV, three independent full-length cDNA clones which contain segment A of serotype I strain D78 or serotype II strain 23/82 and segment B of the serotype I strain P2, respectively, were constructed. Synthetic RNAs of segments A and B were produced by in vitro transcription reaction on linearized plasmids with T7 RNA polymerase. Transcripts of these segments, either untreated or treated with DNase or RNase, were evaluated for the generation of infectious virus by transfection of Vero cells.

The present inventors have demonstrated that synthetic transcripts derived from cloned DNA corresponding to the entire genome of a segmented dsRNA animal virus can give rise to a replicating virus. The recovery of infectious virus after transfecting cells with synthetic plus-sense RNAs derived from cloned cDNA of a virus with a dsRNA genome (IBDV) completes the quest of generating reverse infectious systems for RNA viruses. A number of investigators have generated infectious animal RNA viruses from cloned cDNA (Boyer, J. C., et al., *Virology*, 198, 415–426 (1994)). Van der Werf et al. were first to generate poliovirus, a plus-stranded RNA virus, using synthetic RNA produced by T7 RNA polymerase on cloned cDNA template (van der Werf, S., et al., *Proc. Natl. Acad. Sci. USA*, 83, 2330–2334 (1986)). later, Enami et al. rescued influenza virus, a segmented negative-stranded RNA virus (Enami, M., et al., *Proc. Natl. Acad. Sci. USA*, 87, 3802–3805 (1990)); and Schnell et al. generated rabies virus, a non-segmented negative-stranded RNA virus, from cloned cDNAs of their respective genomes (Schnell, M. J., et al., *EMBO J.*, 13, 4195–4205 (1994)). Roner et al. developed an infectious system for a segmented dsRNA reovirus by transfecting cells with a combination of synthetic ssRNA, dsRNA, in vitro translated reovirus products, and complemented with a helper virus of different serotype (Roner, M. R., et al., *Virology*, 179, 845–852 (1990)). The resulting virus was discriminated from the helper virus by plaque assay. However, in this system the use of a helper virus was necessary. In contrast, the presently described reverse genetics system of IBDV does not require a helper virus or other viral proteins. Transfection of cells with plus-sense RNAs of both segments was sufficient to generate infectious virus (IBDV). The fate of the additional one or four nucleotides, respectively, transcribed at the 3'-end of segment A was not determined. However, this did not prevent the replication of the viral dsRNA. Similar effects were observed for plus-stranded RNA viruses by different investigators (Boyer, J. C., et al., *Virology*, 198, 415–426 (1994)).

Transfection of plus-sense RNAs of both segments into the same cell was necessary for the successful recovery of IBDV. Transfected RNAs of both segments had to be translated by the cellular translation machinery. The polyprotein of segment A was presumably processed into VP2, VP3 and VP4 proteins which form the viral capsid. The translated protein VP1 of segment B probably acted as a RNA-dependent RNA polymerase and transcribed minus-strands from synthetic plus-strands of both segments, and the reaction products formed dsRNA. Recently, Dobos reported that in vitro transcription by the virion RNA-dependent RNA polymerase of infectious pancreatic necrosis virus (IPNV), a prototype virus of the Birnaviridae family, is primed by VP1 and then proceeds via an asymmetric, semiconservative, strand-displacement mechanism to synthesize only plus strands during replication of the viral genome (Dobos, P., *Virology*, 208, 10–25 (1995)). The present system shows that synthesis of minus-strands proceeds on the plus-strands. Whether the resulting transcribed minus-strand RNA serves as a template for the transcription of plus-strands or not remains the subject of further investigation.

To prove that the infectious IBDV contained in the supernatants of transfected cells was indeed derived from the synthetic transcripts, an artificial chimera was generated containing segment A of a serotype II strain and segment B of a serotype I strain. Sequence analysis verified this genome combination. The results also indicate that the terminal sequence motifs described by Mundt and Muller are probably responsible for replication, sorting and packaging of the viral genome (Mundt, E. et al., *Virology*, 209, 10–18 (1995)). Presence of serotype-specific terminal sequences obviously does not prevent proper replication of serotype II A segment by the action of the RNA-dependent RNA polymerase VP1 of the serotype I segment B. The ability to create recombinant viruses will greatly help in analyzing the precise function of serotype-specific and serotype-common terminal sequences.

The recovery of infectious IBDV demonstrates that only the plus-strand RNAs of both segments are sufficient to initiate replication of dsRNA. Thus, the results are in agreement with the general features of reovirus and rotavirus replication where the plus-strand RNAs serve as a template for the synthesis of progeny minus-strands to yield dsRNA (Schonberg, M., et al., *Proc. Natl. Acad. Sci.* Patton, J. T., *Virus Res.*, 6, 217–233 (1986); Chen, D., et al., *J. Virol.*, 68, 7030–7039 (1994)). However, the semiconservative, strand displacement mechanisms proposed by Spies et al. and Dobos could not be excluded (Spies, U., et al., *Virus Res.*, 8, 127–140 (1987); Dobos, P., *Virology*, 208, 10–25 (1995)). The development of a reverse genetics system for IBDV will greatly facilitate future studies of gene expression, pathogenesis, and help in the design of new generations of live and inactivated IBDV vaccines.

As used in the present application, the term "synthetic" as applied to nucleic acids indicates that it is a man made nucleic acid in contrast to a naturally occurring nucleic acid. The term implies no limitation as to the method of manufacture, which can be chemical or biological as long as the method of manufacture involves the intervention of man.

The term "cDNA" is intended to encompass any cDNA containing segments A and B and the 5' and 3' noncoding regions of segments A and B.

The term "infectious" as applied to viruses indicates that the virus has the ability to reproduce. The virus can be pathogenic or nonpathogentic and still be infectious.

The present invention provides a system for the generation of infectious bursal disease virus using synthetic RNA transcripts. This system can be used to study the regulation of viral gene expression, pathogenesis, and for the design of a new generation of live and inactivated IBDV vaccines.

The present invention provides a recombinant vector containing at least one copy of the cDNA according to the present invention. The recombinant vector may also comprise other necessary sequences such as expression control sequences, markers, amplifying genes, signal sequences, promoters, and the like, as is known in the art. Useful vectors for this purpose are plasmids, and viruses such as baculoviruses, herpes virus (HVT) and pox viruses, e.g., fowl pox virus, and the like.

Also provided herein is a host cell transformed with the recombinant vector of the present invention or a host cell transfected with the synthetic RNA of the present invention. The host cell may be a eukaryotic or a prokaryotic host cell. Suitable examples are *E. coli*, insect cell lines such as Sf-9, chicken embryo fibroblast (CEF) cells, chicken embryo kidney (CEK) cells, African green monkey Vero cells and the like.

Also part of this invention is an IBDV poultry vaccine comprising a poultry protecting amount of a recombinantly produced virus or portion of a virus, wherein the virus is inactivated or modified such that it is no longer virulent.

The virus can be inactivated by chemical or physical means. Chemical inactivation can be achieved by treating the virus with, for example, enzymes, formaldehyde, β-propiolactone, ethylene-imine or a derivative thereof, an organic solvent (e.g. halogenated hydrocarbon) and or a detergent. If necessary, the inactivating substance can be neutralized after the virus has been inactivated. Physical inactivation can be carried out by subjecting the viruses to radiation such as UV light, X-radiation, or γ-radiation.

The virus can be attenuated by known methods including serial passage, deleting sequences of nucleic acids and site directed mutagenesis either before or after production of the infectious virus to produce a virus which retains sufficient antigenicity but which has reduced virulence.

Physiologically acceptable carriers for vaccination of poultry are known in the art and need not be further described herein. In addition to being physiologically acceptable to the poultry the carrier must not interfere with the immunological response elicited by the vaccine and/or with the expression of its polypeptide product.

Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IBDV. The amount of adjuvant added to the vaccine will vary depending on the nature of the adjuvant, generally ranging from about 0.1 to about 100 times the weight of the IBDV, preferably from about 1 to about 10 times the weight of the IBDV.

The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

The vaccine can be administered by any suitable known method of inoculating poultry including nasally, ophthalmically, by injection, in drinking water, in the feed, by exposure, and the like. Preferably, the vaccine is administered by mass administration techniques such as by placing the vaccine in drinking water or by spraying the animal' environment. When administered by injection, the vaccines are preferably administered parenterally. Parenteral administration as used herein means administration by intravenous, subcutaneous, intramuscular, or intraperitoneal injection.

The vaccine of the present invention is administered to poultry to prevent IBD anytime before or after hatching. Preferably, the vaccine is administered prior to the time of birth and after the animal is about 6 weeks of age. Poultry is defined to include but not be limited to chickens, roosters, hens, broilers, roasters, breeders, layers, turkeys and ducks.

The vaccine may be provided in a sterile container in unit form or in other amounts. It is preferably stored frozen, below −20° C., and more preferably below −70° C. It is thawed prior to use, and may be refrozen immediately thereafter. For administration to poultry the recombinantly produced virus may be suspended in a carrier in an amount of about $10^4$ to $10^7$ pfu/ml, and more preferably about $10^5$ to $10^6$ pfu/ml in a carrier such as a saline solution. The inactivated vaccine may contain the antigenic equivalent of $10^4$ to $10^7$ pfu/ml suspended in a carrier. Other carriers may also be utilized as is known in the art. Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, eye drops, nose drops, and the like.

The invention also can be used to produce combination vaccines with the IBDV material. The IBDV material can be combined with antigen material of Newcastle Disease Virus Infectious Bronchitis virus, Reo virus, Adeno virus and/or the Marek virus.

The foregoing embodiments of the present invention are further described in the following Examples. However, the present invention is not limited by the Examples, and variations will be apparent to those skilled in the art without departing from the scope of the present invention.

BRIEF DESCRIPTION OF THE DRAWINGS

FIG. 3 shows a comparison of nucleotide sequences of cloned RT-PCR fragments from segments A and B of the chimeric IBDV strain 23A/P2B (bold-typed) with known sequences of segments A and B of serotype II strain 23/82 and serotype I strain P2, respectively. Nucleotide identities are marked by a colon.

FIG. 4 shows the DNA sequence of pUC18FLA23.

FIG. 5 shows the DNA sequence of pUC19FLAD78.

FIG. 6 shows the DNA sequence of pUC18FLBP2.

EXAMPLES

Viruses and Cells. Two serotype I strains of IBDV, the attenuated P2 strain from Germany and the vaccine strain D78 (Intervet International), and one serotype II strain, the apathogenic 23/82 strain, were propagated in chicken embryo cells (CEC) and purified (Mundt, E. et al., *Virology*, 209, 10–18 (1995); Vakharia, V. N., et al., *Virus Res.*, 31, 265–273 (1994)). Vero cells were grown in M199 medium supplemented with 5% fetal calf serum (FCS) and used for transfection experiments. Further propagation of the recovered virus and immunofluorescence studies were carried out in Vero cells (Mundt, E., et al., *J. Gen. Virol.*, 76, 437–443, (1995)). For plaque assay, monolayers of secondary CEC were prepared and used (Müller, H., et al., *Virus Res.*, 4, 297–309 (1986)).

Figure 1A:
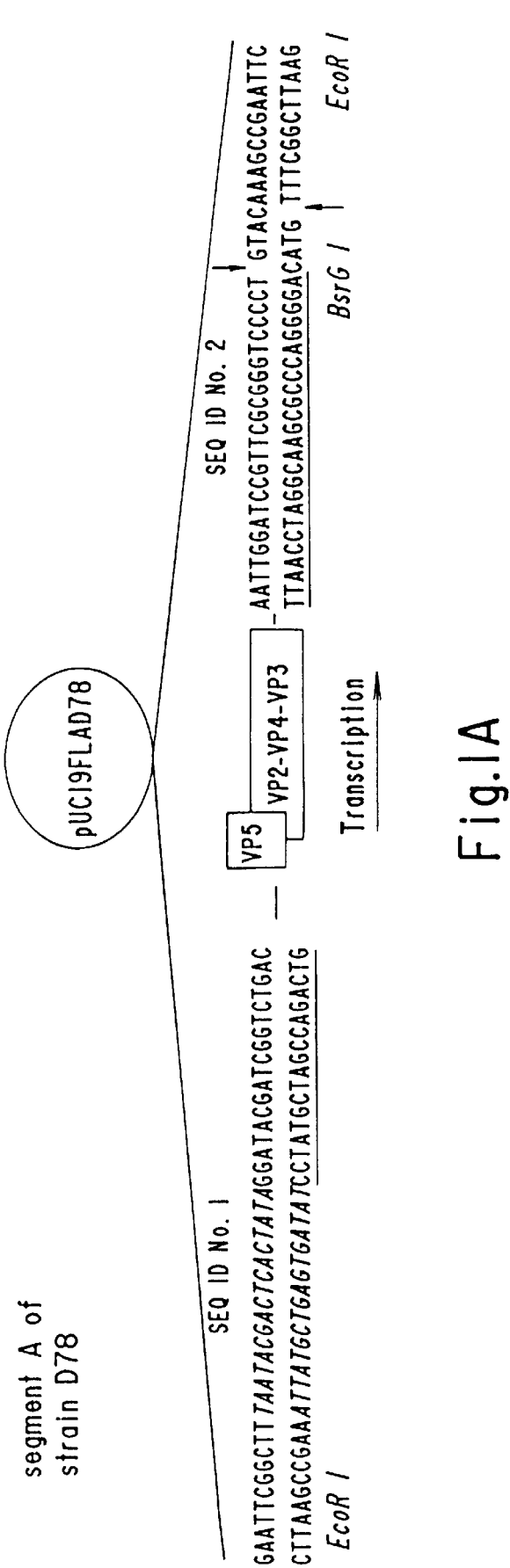
FIG. 1 is a schematic diagram of cDNA constructs used for synthesis of plus-sense ssRNAs of IBDV with T7 RNA polymerase. Construct pUC19FLAD78 contains the cDNA of segment A of IBDV strain D78 and the recombinant plasmid pUC18FLA23 contains the full-length cDNA of segment A of IBDV strain 23/82. Segment A of IBDV encodes the polyprotein (VP2-VP4-VP3), and the recently identified VP5 protein. Plasmid pUC18FLBP2 contains the cDNA of segment B of strain P2 which encodes the RNA-dependent RNA polymerase (VP1). Virus specific sequences are underlined and the T7 promoter sequences are italicized. Restriction sites are shown in boldface and identified. The cleavage sites of the linearized plasmids are shown by vertical arrows and the transcription directions are marked by horizontal arrows.

Construction of Full-Length cDNA Clones of IBDV genome. Full-length cDNA clones of IBDV segments A and B were independently prepared. The cDNA clones containing the entire coding region of the RNA segment A of strain D78 were prepared using standard cloning procedures and methods (Vakharia, V. N., et al., *Virus Res.*, 31, 265–273 (1994)). By comparing the D78 terminal sequences with recently published terminal sequences of other IBDV strains (Mundt, E. et al., *Virology*, 209, 10–18 (1995)), it was observed that D78 cDNA clones lacked the conserved first 17 and last 10 nucleotides at the 5'-and 3'-ends, respectively. Therefore, to construct a full-length cDNA clone of segment A, two primer pairs (A5'-D78, A5-IPD78 and A3'-IPD78) were synthesized and used for PCR amplification (Table 1). The DNA segments were amplified according to the protocol of the supplier (New England Biolabs) using "Deep Vent Polymerase" (high fidelity thermophilic DNA polymerase). Amplified fragments were cloned into the EcoR I site of a pCRII vector (Invitrogen Corp.) to obtain plasmids pCRD78A5' and pCRD78A3', respectively. Each plasmid was digested with EcoR I and Sal I and the resultant fragments were ligated into EcoR I digested pUC19 to obtain plasmid pUC19FLAD78 (SEQ ID NOS:27 AND 29) which now contains a full-length cDNA copy of segment A encoding all the structural proteins (VP2, VP4 and VP3, SEQ ID NO:30) as well as the non-structural VP5 protein (SEQ ID NO:28) (FIG. 1).

Two primer pairs (A5'-23, A5IP23 and A3'-23, A3-IP23; see Table 1) were used for reverse transcription (RT) of viral genomic dsRNA of strain 23/82 using "SuperScript RT II" (RNA directed DNA polymerase with reduced RNase H activity, GIBCO/BRL). The RT reaction products were purified by phenol/chloroform extraction and ethanol precipitation. To obtain two cDNA fragments bounded by primer pairs A5'-23, A5-IP23 and A3'-23, A3-IP23, respectively, RT reaction products were amplified by PCR using "Deep Vent polymerase". Both RT and PCR were carried out according to the supplier's protocol. Resulting PCR fragments were blunt-end ligated into Sma I cleaved pUC18 vector to obtain pUC23A5' and pUC23A3'. The 3'-end of segment A contained in plasmid pUC23A3' was ligated into the Hind III-BstB I cleaved plasmid pUC23A5' to establish the full-length cDNA of segment A of strain 23/82. The resulting plasmid was termed pUC18FLA23 (SEQ ID NOS: 31 AND 33)(FIG. 1) and encodes structural proteins VP2, VP3 and VP4 (SEQ ID NO: 32) and non-structural protein VP5 (SEQ ID NO: 34)

To obtain cDNA clones of segment B of P2 strain, two primer pairs (B5'-P2, B5-IPP2 and B3'-P2, B3-IPP2) were designed according to the published sequences and used for RT-PCR amplification (see Table 1). Using genomic dsRNA as template, cDNA fragments were synthesized and amplified according to the supplier's protocol (Perkin-Elmer Cetus). Amplified fragments were blunt-end ligated into Sma I cleaved pBS vector (Stratagene) to obtain clones pBSP2B5' and pBSP2B3'. To construct a full-length clone of segment B, the 5'-end fragment of plasmid pBSP2B5' was first subcloned between EcoR I and Pst I sites of pUC18 vector to obtain pUCP2B5'. Then the 3'-end fragment of plasmid pBSP2B3' was inserted between the unique Bgl II and Pst I sites of plasmid pUCP2B5' to obtain a full-length plasmid pUC18FLBP2 (SEQ ID NO:25) which encodes the VP1 protein (SEQ ID NO: 26) (FIG. 1). Plasmids pUC18FLBP2, pUC18FLA23 and pUC19FLAD78 were completely sequenced by using the "Sequenase" DNA sequencing system (U.S. Biochem.), and the sequence data were analyzed using either "DNASIS" (Pharmacia) or "PC/Gene" (Intelligenetics) software. The integrity of the full-length constructs was tested by in vitro transcription and translation coupled reticulocyte lysate system using T7 RNA polymerase (Promega).

Transcription and Transfection of Synthetic RNAs. Plasmids pUC19FLAD78, pUC18FLA23 and pUC18FLBP2 were digested with BsrG I, Nsi I and Pst I enzymes (see FIG. 1), respectively, and used as templates for in vitro transcription with T7 RNA polymerase (Promega). Briefly, restriction enzyme cleavage assays were adjusted to 0.5% SDS and incubated with proteinase K (0.5 mg/ml) for 1 hour at 37° C. The linearized DNA templates (~3 µg) were recovered after ethanol precipitation, and were added separately to a transcription reaction mixture (50 µl) containing 40 mM Tris-HCl (pH 7.9), 10 mM NaCl, 6 mM $MgCl_2$, 2 mM spermidine, 0.5 mM ATP, CTP and UTP each, 0.1 mM GTP, 0.25 mM cap analog [m7G(5') PPP(5') G], 120 units of "RNasin" (ribonuclease inhibitor), 150 units T7 RNA polymerase (Promega), and incubated at 37° C. for 1 hour. Synthetic RNA transcripts were purified by phenol/chloroform extraction and ethanol precipitation. As controls, the transcription products were treated with either DNase or RNase (Promega) before the purification step.

Vero cells were grown to 80% confluence in 60 mm dishes and washed once with phosphate-buffered saline (PBS). Three ml of "OPTI-MEM I" (reduced serum medium containing HEPES buffer, sodium bicarbonate, hypoxanthine, thymidine, sodium pyruvate, L-glutamine, trace elements, growth factors and phenol red; from GIBCO/BRL) were added to the monolayers, and the cells were incubated at 37° C. for 1 hour in a $CO_2$ incubator. Simultaneously, 0.15 ml of "OPTI-MEM I" was incubated with 1.25 µg of "Lipofectin" reagent (N-[1-(2,3-dioleyloxy)propyl]-N,N,N-trimethylammonium chloride and dioleoylphosphatidylethanolamine, GIBCO/BRL) for 45 min. in a polystyrene tube at room temperature. Synthetic RNA transcripts of both segments, resuspended in 0.15 ml of diethyl pyrocarbonate-treated water, were added to the OPTI-MEM-Lipofectin-mixture, mixed gently, and incubated on ice for 5 min. After removing the "OPTI-MEM" from the monolayers in 60 mm dishes and replacing with fresh 1.5 ml of "OPTI-MEM", the nucleic acid containing mixture was added drop-wise to the Vero cells and swirled gently. After 2 hours of incubation at 37° C., the mixture was replaced with M199 medium [$CaCl_2$ (annhydrous), $Fe(NO_3)_3 9H_2O$, KCl, $MgSO_4$ (anhydrous), NaCl, $NaH_2PO_4H_2O$, $NaHCO_3$, L-Alanine, L-Arginine HCl, L-Aspartic acid, L-Cysteine HCl $H_2O$, L-Cysteine 2HCl, L-Glutamic acid, L-Glutamine, Glycine, L-Histidine HCL $H_2O$, L-Hydroxyproline, L-Isoleucine, L-Leucine, L-Lysine HCl, L-Methionine, L-Phenylalanine, L-Proline, L-Serine, L-Threonine, L-Tryptophan, L-Tyrosine 2Na $2H_2O$, L-Valine, Alpha tocopherol $PO_4$ $Na_2$, Ascorbic Acid, Biotin, Calciferol, D-Calcium pantothenate, Choline chloride, Folic acid, I-Inositol, Menandione $NaHSO_3 3H_2O$, Niacin, Nicotinamide, Para-aminobenzoic acid, Pyridoxine HCl, Riboflavin, Thiamine HCl, Vitamin A Acetate, Adenine SO4, Adenylic Acid, ATP, $Na_2$, Cholesterol, 2-Deoxy-D-Ribose, D-Glucose, Glutathione, Guanine HCl, Hypoxanthine Na, Phenol Red Na, Ribose, Sodium Acetate (anhydrous), Thymine, Tween 80, Uracil, and Xanthine Na; from Mediatech, Inc.] containing 5% FCS (without rinsing cells) and the cells were further incubated at 37° C. for desired time intervals.

Identification of Generated IBDV. CEC were infected with filtered (0.2 µm) supernatant from Vero cells transfected with transcripts of pUC18FLA23 and pUC18FLP2B. 16 hours post-infection, the whole cell nucleic acids were isolated (Mundt, E. et al., Virology, 209, 10–18 (1995)). Primers were designed according to the published sequences and RT-PCR fragments were amplified, cloned and sequenced (Mundt, E. et al., Virology, 209, 10–18 (1995)). Sequence data were analyzed by using "DNASIS" software.

Immunofluorescence. Vero cells, grown on cover slips to 80% confluence, were infected with the supernatants derived from transfected Vero cells (after freeze-thawing) and incubated at 37° C. for two days. The cells were then washed, fixed with acetone and treated with polyclonal rabbit anti-IBDV serum. After washing, the cells were treated with fluorescein labeled goat-anti-rabbit antibody (Kirkegaard & Perry Lab.) and examined by fluorescence microscope.

Plaque Assay. Monolayers of secondary CEC, grown in 60 mm dishes, were inoculated with the supernatants derived from transfected Vero cells. After 1 hour of infection, the cells were washed once with PBS and overlayed with 0.8% Agar noble (Difco) containing 10% tryptose phosphate broth, 2% FCS, 0.112% $NaHCO_3$, $10^3$ units penicillin, $10^3$ µg/ml streptomycin, 0.25 µg/ml fungizone, 0.005% neutral red, 0.0015% phenol red. The cells were incubated at 37° C. for 2 to 3 days until plaques could be observed and counted (Müller, H., et al., Virus Res., 4, 297–309 (1986)).

Construction of Full-Length cDNA clones of IBDV Genome. To develop a reverse genetics system for the dsRNA virus IBDV, two independent cDNA clones were constructed that contain segment A of strain D78 and segment B of strain P2 (FIG. 1). Each plasmid encoded either the precursor of structural proteins (VP2, VP4, VP3) and VP5 or only VP1 protein (RNA-dependent RNA polymerase). Plasmid pUC18FLBP2 upon digestion with Pst I and transcription in vitro by T7 RNA polymerase, would yield RNA containing the correct 5'- and 3'-ends. Whereas, upon digestion with BsrG I and transcription, plasmid pUC19FLAD78 would yield RNA containing the correct 5'-end but with additional four nucleotides at the 3' end. Coupled transcription and translation of the above plasmids in a rabbit reticulocyte system yielded protein products that were correctly processed and comigrated with the marker IBDV proteins after fractionating on SDS-polyacrylamide gel and autoradiography (data not shown).

Figure 2:
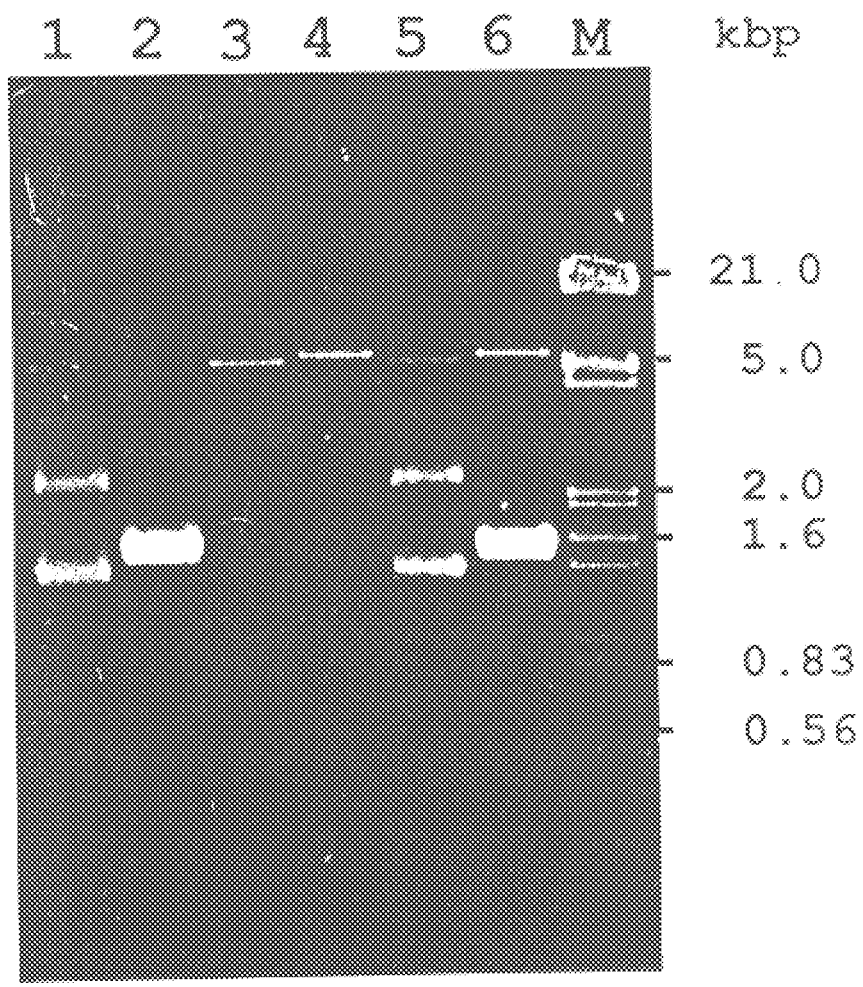
FIG. 2 shows an agarose gel analysis of the transcription reaction products that were used for transfection of Vero cells. Synthetic RNAs transcribed in vitro using T7 RNA polymerase and linearized plasmids pUC19FLAD78 (lanes 2, 4 and 6) containing the cDNA of segment A of IBDV strain D78, and pUC18FLBP2 (lanes 1, 3 and 5) containing the cDNA of segment B of strain P2, respectively. After transcription, the reaction mixtures were either treated with DNase (lanes 1 and 2), RNase (lanes 3 and 4) or left untreated (lanes 5 and 6). Two μl of the reaction products were analyzed on 1% agarose gel. Lambda DNA, digested with Hind III/EcoR I, was used as markers (lane M).

Transcription, Transfection and Generation of Infectious Virus. Plus-sense transcripts of IBDV segment A and B were synthesized separately in vitro with T7 RNA polymerase using linearized full-length cDNA plasmids as templates (see FIG. 2). Although two species of RNA transcripts were observed for segment B on a neutral gel (lanes 1 and 5), fractionation of these samples on a denaturing gel yielded only one transcript-specific band (data not shown). In order to show that plus-sense RNA transcripts of both segments are needed for the generation of infectious virus, the transcription mixtures were incubated with different nucleases, as shown in FIG. 2. Synthetic RNAs recovered after treating the transcription products with DNase (lanes 1+2), RNase (lanes 3+4) or without treatment (lanes 5+6), were used for the transfection of Vero cells. As mock control, Lipofectin alone was used. Five days post-transfection, cytopathic effect (CPE) was only visible in Vero cells transfected with combined transcripts of untreated or DNase-treated transcription products, but not with RNase-treated transcription mixtures or mock-transfected control. In addition, no CPE was detected when Vero cells were transfected with RNA of only segment A or B (data not shown). These results demonstrate that replication of IBDV ensued after transfection of Vero cells with plus-sense ssRNAs of both segments of IBDV. To verify that the agent causing the CPE in Vero cells was indeed IBDV, transfected Vero cells were freeze-thawed, and supernatants were clarified by centrifugation, and used to infect CEC or Vero cells. CEC infected with the supernatants derived from Vero transfected cells of untreated or DNase-treated transcription mixtures produced CPE in one day post-inoculation (Table 2). However, no CPE could be detected even after five days in CEC, with the supernatants from transfected Vero cells of RNase-treated transcription mixtures, untreated segment A or B transcription mixtures and mock-transfected Vero cells. Similarly, when Vero cells on cover slips were infected with the same supernatants as described above and examined by immunofluorescence staining after 2 days, only supernatants derived from transfected Vero cells of untreated or DNAse-treated transcription mixtures gave positive immunofluorescence signal (Table 2).

Recovery of Transfectant Virus. To determine the time point for the recovery of infectious virus, Vero cells were transfected with combined RNA transcripts of segments A and B. At 4, 8, 16, 24, 36 and 48 hours post-transfection, the supernatants were examined for the presence of transfectant virus by infectivity and plaque assays, as shown in Table 3. Our results indicate that the virus could be recovered as early as 36 hours after transfection. Virus titer was $2.3 \times 10^2$ pfu/ml which appear to drop for samples obtained later than 48 hours after transfection.

Generation of a Chimeric Virus. To prove that plus-sense ssRNA of both segments of IBDV are sufficient for recovery of infectious virus, a chimeric IBDV was generated. Plasmid pUC18FLA23 containing a full-length sequence of segment A of serotype II strain was linearized by Nsi I digestion and ssRNA was synthesized in vitro using T7 RNA polymerase. The ssRNA transcript specifies the correct 5'-end but contains one additional residue at the 3'-end (FIG. 1). Vero cells were transfected with ssRNA of segment A of serotype II strain 23/82 and ssRNA of segment B of serotype I strain P2. Five days after transfection when CPE was evident, the supernatant was clarified (after freeze-thawing) and used to infect CEC. After a second passage in CEC, genomic RNA of the virus was analyzed by RT-PCR and sequencing of the PCR products. Primers for segment A were deigned to specifically amplify only segment A sequences derived from the serotype II strain. Primer for segment B bound to sequences of both serotypes. The amplified fragments were cloned and sequenced. The obtained segment A sequences showed a perfect match with known segment A sequences of serotype II strain 23/82, whereas segment B sequence exhibited complete homology to published segment B sequences of serotype I strain P2 (FIG. 3).

TABLE 1

Oligonucleotides Used for the Construction of Full-Length cDNA Clones of IBDV Genomic Segments A and B.

| Nucleotide Sequence | Orientation | Name | Nucleotide Number |
|---|---|---|---|
| SEQ ID NO: 13<br>TAATACGACTCACTATAGGATACGATCGGTCTGACCCCGGGGAGTCA | (+) | A5'-D78 | 1–31 |
| SEQ ID NO: 14<br>AGAGAATTCTAATACGACTCACTATAGGATACGATCGGTCTGAC | (+) | A5'-23 | 1–18 |
| SEQ ID NO: 15<br>TGTACAGGGGACCCGCGAACGGATCCAATT | (−) | A3'-D78 | 3237–3261 |
| SEQ ID NO: 16<br>CGGCGAATTCATGCATAGGGGACCCGCGAACGGATC | (−) | A3'-23 | 3242–3261 |
| SEQ ID NO: 17<br>CGTCGACTACGGGATTCTGG | (−) | A5-IPD78 | 1711–1730 |
| SEQ ID NO: 18<br>CAGAGGCAGTACTCCGTCTG | (−) | A5-IP23 | 1971–1990 |
| SEQ ID NO: 19<br>AGTCGACGGGATTCTTGCTT | (+) | A3-IPD78 | 1723-1742 |
| SEQ ID NO: 20<br>GAAGGTGTGCGAGAGGAC | (+) | A3-IP23 | 1883–1900 |
| SEQ ID NO: 21<br>AGAGAATTCTAATACGACTCACTATAGGATACGATGGGTCTGAC | (+) | B5'-P2 | 1–18 |
| SEQ ID NO: 22<br>CGATCTGCTGCAGGGGGCCCCCGCAGGCGAAGG | (−) | B3'-P2 | 2807–2827 |
| SEQ ID NO: 23<br>CTTGAGACTCTTGTTCTCTACTCC | (−) | B5-IPP2 | 1915–1938 |
| SEQ ID NO: 24<br>ATACAGCAAAGATCTCGGG | (+) | B3-IPP2 | 1839–1857 |

Composition and location of the oligonucleotide primers used for cloning. T7 promoter sequences are marked with italic types, the virus specific sequences are underlined, and the restriction sites marked in boldface. Orientation of the virus specific sequence of the primer is shown for sense (+) and antisense (−). The positions where the primers bind (nucleotide number) are according to the published sequences of P2 strain (2).

TABLE 2

Generation of Infectious IBDV From Synthetic RNAs of Segment A and B.

| Material Transfected | CPE | Immunofluorescence |
|---|---|---|
| ssRNA A + B, DNase-treated | + | + |
| ssRNA A + B, RNase-treated | − | − |
| ssRNA A + B, untreated | + | + |
| ssRNA A, untreated | − | − |
| ssRNA B, untreated | − | − |
| Lipofectin only | − | − |

Vero cells were transfected with synthetic RNAs of segment A and B derived from transcription reactions that were either untreated or treated with DNase or RNase. After 5 days, the supernatants were collected, clarified by centrifugation and analyzed for the presence of virus. The infectivity of the recovered virus was detected in CEC by the appearance of cytopathic effect (CPE) 1–2 days post-inoculation. The specificity of the recovered virus was determined by immunofluorescence staining of infected Vero cells with rabbit and IBDV serum.

TABLE 3

Recovery of Virus at Various Times Post-Transfection.

| Time in hours post-transfection | CPE | Immunofluorescence | pfu/ml |
|---|---|---|---|
| 4 | − | − | 0 |
| 8 | − | − | 0 |
| 16 | − | − | 0 |
| 24 | − | − | 0 |
| 36 | + | + | $2.3 \times 10^2$ |
| 48 | + | + | $6.0 \times 10^1$ |

Vero cells were transfected with synthetic RNAs of segment A and B as described. The infectivity and specificity of the recovered virus was detected by CPE in CEC and immunofluorescence staining in Vero cells, respectively. Monolayers of secondary CEC were used for plaque assay after inoculating the cells with the supernatants derived from transfected Vero cells. Approximate titer of the virus was calculated as plaque forming units per ml (pfu/ml).

We claim:

1. A method for preparing live Birnavirus, comprising the following steps:

preparing one or more cDNAs of Birnavirus genome segments A and B, transcribing said one or more cDNAs to produce synthetic RNA transcripts, wherein said RNA transcripts are plus sense RNA transcripts of said segments A and B, transfecting host cells with said synthetic RNA transcripts, incubating said host cells in a culture medium, and isolating live infectious Birnavirus from said culture medium.

2. The method according to claim 1, wherein said Birnavirus is Infectious Bursal Disease Virus (BDV).

3. The method according to claim 1, wherein said host cells are African green monkey Vero cells.

4. The method according to claim 1, wherein said Birnavirus genome segments A and B are independently prepared from different strains of Birnavirus.

5. The method according to claim 4, wherein said segment A is present in plasmid pUC19FLAD78 or pUC18FLA23.

6. The method according to claim 4, wherein said segment B is present in plasmid pUC18FLBP2.

7. A live chimeric Infectious Bursal Disease Virus (IBDV), wherein said virus is made by a process comprising the steps of
- preparing one or more cDNAs of infectious bursal disease virus genome segments A and B, wherein said cDNAs are derived from more than one strain of infectious bursal disease virus,
- transcribing said one or more cDNAs to produce synthetic RNA transcripts, wherein said RNA transcripts are plus sense RNA transcripts of said segments A and B,
- transfecting a host cell with said synthetic RNA transcripts,
- incubating said host cell in a culture medium, and
- isolating live, chimeric, Infectious Bursal Disease Virus (IBDV) from said culture medium.

8. A plasmid selected from the group consisting of pUC19FLAD78, pUC18FLA23, and pUC19FLBP2.

9. A host cell transformed with the vector according to claim 11.

10. A vaccine comprising a live chimeric Infectious Bursal Virus (IBDV) according to claim 7, wherein said live chimeric Infectious Bursal Disease Virus (IBDV) is inactivated prior to administration.

11. The method according to claim 1, wherein said host cells are poultry cells.

12. The method according to claim 11, wherein said poultry cells are chicken, turkey, or quail cells.

13. The method according to claim 12, wherein said poultry cells are chicken embryo fibroblast cells or chicken embryo kidney cells.

14. The live chimeric Infectious Bursal Disease Virus (IBDV) according to claim 7, wherein said live chimeric Infectious Bursal Disease Virus (IBDV) genome segments A and B are independently prepared from different strains of IBDV.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 46 base pairs
        ( B ) TYPE: nucleic acid ( C ) STRANDEDNESS: double
( D ) TOPOLOGY: circular ( i i ) MOLECULE TYPE: cDNA ( x i ) SEQUENCE DESCRIPTION: SEQ ID NO:1:

GAATTCGGCT TTAATACGAC TCACTATAGG ATACGATCGG TCTGAC     46

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:2:

AATTGGATCC GTTCGCGGGT CCCCTGTACA AAGCCGAATT C     41

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:3:

CGGCGAATTC ATGCATAGGG GACCCGCGAA CGGATC     36

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:4:

GTCAGACCGA TCGTATCCTA TAGTGAGTCG TATTAGAATT CTCT     44

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:5:

TTGCATGCCT GCAGGGGGCC CCCGCAGGCG AAG     33

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:6:

TCGTATCCTA TAGTGAGTCG TATTAGAATT C  31

( 2 ) INFORMATION FOR SEQ ID NO:7:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

GGAAGCCTGA GTGAGTTGAC TGACTACAGC TACAACGGGC TGATGTCAGC CACTGCGAAC  60

ATCAACGACA AGATCGGGAA CGTTCTAGTT GGAGAAGGGG TGACTGTTCT CAGTCTACCG  120

( 2 ) INFORMATION FOR SEQ ID NO:8:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GGAAGCCTGA GTGAGTTGAC TGACTACAGC TACAACGGGC TGATGTCAGC CACTGCGAAC  60

ATCAACGACA AGATCGGGAA CGTTCTAGTT GGAGAAGGGG TGACTGTTCT CAGTCTACC  119

( 2 ) INFORMATION FOR SEQ ID NO:9:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GGAAGCCTGA GTGAACTGAC AGATGTTAGC TACAATGGGT TGATGTCTGC AACAGCCAAC  60

ATCAACGACA AAATTGGGAA CGTCCTAGTA GGGGAAGGGG TCACCGTCCT CAGCTTACCC  120

( 2 ) INFORMATION FOR SEQ ID NO:10:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TTTTCAATAG TCCACAGGCG CGAACGAAGA TCTCAGCAGC GTTCGGCATA AAGCCTACTG  60

CTGGACAAGA CGTGGAAGAA CTCTTGATCC CCAAAGTCTG GGTGCCACCT GAGGATCCGC  120

( 2 ) INFORMATION FOR SEQ ID NO:11:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TTTTCAACAG TCCACAGGCG CGAAGCACGA TCTCAGCAGC GTTCGGCATA AAGCCTACTG        60

CTGGACAAGA CGTGGAAGAA CTCTTGATCC CTAAAGTTTG GGTGCCACCT GAGGATCCGC       120

( 2 ) INFORMATION FOR SEQ ID NO:12:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TTTTCAACAG TCCACAGGCG CGAAGCACGA TCTCAGCAGC GTTCGGCATA AAGCCTACTG        60

CTGGACAAGA CGTGGAAGAA CTCTTGATCC CTAAAGTTTG GGTGCCACCT GAGGATCCGC       120

( 2 ) INFORMATION FOR SEQ ID NO:13:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

TAATACGACT CACTATAGGA TACGATCGGT CTGACCCCGG GGGAGTCA        48

( 2 ) INFORMATION FOR SEQ ID NO:14:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AGAGAATTCT AATACGACTC ACTATAGGAT ACGATCGGTC TGAC        44

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

TGTACAGGGG ACCCGCGAAC GGATCCAATT        30

( 2 ) INFORMATION FOR SEQ ID NO:16:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

CGGCGAATTC ATGCATAGGG GACCCGCGAA CGGATC    36

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

CGTCGACTAC GGGATTCTGG    20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

CAGAGGCAGT ACTCCGTCTG    20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

AGTCGACGGG ATTCTTGCTT    20

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

GAAGGTGTGC GAGAGGAC    18

( 2 ) INFORMATION FOR SEQ ID NO:21:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

AGAGAATTCT AATACGACTC ACTATAGGAT ACGATGGGTC TGAC    44

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

```
CGATCTGCTG CAGGGGGCCC CCGCAGGCGA AGG                                    33
```

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

```
CTTGAGACTC TTGTTCTCTA CTCC                                              24
```

( 2 ) INFORMATION FOR SEQ ID NO:24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

```
ATACAGCAAA GATCTCGGG                                                    19
```

( 2 ) INFORMATION FOR SEQ ID NO:25:

( i ) SEQUENCE CHARACTERISTICS:
        ( A ) LENGTH: 2827 base pairs
        ( B ) TYPE: nucleic acid
        ( C ) STRANDEDNESS: single
        ( D ) TOPOLOGY: circular ( i i ) MOLECULE TYPE: cDNA ( i x ) FEATURE:
        ( A ) NAME/KEY: CDS
        ( B ) LOCATION: 112..2745

( x i ) SEQUENCE DESCRIPTION: SEQ ID NO:25:

```
GGATACGATG GGTCTGACCC TCTGGGAGTC ACGAATTAAC GTGGCTACTA GGGGCGATAC        60

CCGCCGCTGG CCGCCACGTT AGTGGCTCCT CTTCTTGATG ATTCTGCCAC C ATG AGT        117
                                                        Met Ser
                                                          1

GAC ATT TTC AAC AGT CCA CAG GCG CGA AGC ACG ATC TCA GCA GCG TTC        165
Asp Ile Phe Asn Ser Pro Gln Ala Arg Ser Thr Ile Ser Ala Ala Phe
        5               10                  15

GGC ATA AAG CCT ACT GCT GGA CAA GAC GTG GAA GAA CTC TTG ATC CCT        213
Gly Ile Lys Pro Thr Ala Gly Gln Asp Val Glu Glu Leu Leu Ile Pro
    20              25                  30

AAA GTT TGG GTG CCA CCT GAG GAT CCG CTT GCC AGC CCT AGT CGA CTG        261
Lys Val Trp Val Pro Pro Glu Asp Pro Leu Ala Ser Pro Ser Arg Leu
35              40                  45                  50
```

```
GCA AAG TTC CTC AGA GAG AAC GGC TAC AAA GTT TTG CAG CCA CGG TCT      309
Ala Lys Phe Leu Arg Glu Asn Gly Tyr Lys Val Leu Gln Pro Arg Ser
        55                      60                      65

CTG CCC GAG AAT GAG GAG TAT GAG ACC GAC CAA ATA CTC CCA GAC TTA      357
Leu Pro Glu Asn Glu Glu Tyr Glu Thr Asp Gln Ile Leu Pro Asp Leu
            70                      75                      80

GCA TGG ATG CGA CAG ATA GAA GGG GCT GTT TTA AAA CCC ACT CTA TCT      405
Ala Trp Met Arg Gln Ile Glu Gly Ala Val Leu Lys Pro Thr Leu Ser
                85                      90                      95

CTC CCT ATT GGA GAT CAG GAG TAC TTC CCA AAG TAC TAC CCA ACA CAT      453
Leu Pro Ile Gly Asp Gln Glu Tyr Phe Pro Lys Tyr Tyr Pro Thr His
               100                     105                     110

CGC CCT AGC AAG GAG AAG CCC AAT GCG TAC CCG CCA GAC ATC GCA CTA      501
Arg Pro Ser Lys Glu Lys Pro Asn Ala Tyr Pro Pro Asp Ile Ala Leu
115                     120                     125                 130

CTC AAG CAG ATG ATT TAC CTG TTT CTC CAG GTT CCA GAG GCC AAC GAG      549
Leu Lys Gln Met Ile Tyr Leu Phe Leu Gln Val Pro Glu Ala Asn Glu
                       135                     140                     145

GGC CTA AAG GAT GAA GTA ACC CTC TTG ACC CAA AAC ATA AGG GAC AAG      597
Gly Leu Lys Asp Glu Val Thr Leu Leu Thr Gln Asn Ile Arg Asp Lys
                150                     155                     160

GCC TAT GGA AGT GGG ACC TAC ATG GGA CAA GCA AAT CGA CTT GTG GCC      645
Ala Tyr Gly Ser Gly Thr Tyr Met Gly Gln Ala Asn Arg Leu Val Ala
            165                     170                     175

ATG AAG GAG GTC GCC ACT GGA AGA AAC CCA AAC AAG GAT CCT CTA AAG      693
Met Lys Glu Val Ala Thr Gly Arg Asn Pro Asn Lys Asp Pro Leu Lys
180                     185                     190

CTT GGG TAC ACT TTT GAG AGC ATC GCG CAG CTA CTT GAC ATC ACA CTA      741
Leu Gly Tyr Thr Phe Glu Ser Ile Ala Gln Leu Leu Asp Ile Thr Leu
195                     200                     205                     210

CCG GTA GGC CCA CCC GGT GAG GAT GAC AAG CCC TGG GTG CCA CTC ACA      789
Pro Val Gly Pro Pro Gly Glu Asp Asp Lys Pro Trp Val Pro Leu Thr
                215                     220                     225

AGA GTG CCG TCA CGG ATG TTG GTG CTG ACG GGA GAC GTA GAT GGC GAC      837
Arg Val Pro Ser Arg Met Leu Val Leu Thr Gly Asp Val Asp Gly Asp
            230                     235                     240

TTT GAG GTT GAA GAT TAC CTT CCC AAA ATC AAC CTC AAG TCA TCA AGT      885
Phe Glu Val Glu Asp Tyr Leu Pro Lys Ile Asn Leu Lys Ser Ser Ser
        245                     250                     255

GGA CTA CCA TAT GTA GGT CGC ACC AAA GGA GAG ACA ATT GGC GAG ATG      933
Gly Leu Pro Tyr Val Gly Arg Thr Lys Gly Glu Thr Ile Gly Glu Met
        260                     265                     270

ATA GCT ATC TCA AAC CAG TTT CTC AGA GAG CTA TCA ACA CTG TTG AAG      981
Ile Ala Ile Ser Asn Gln Phe Leu Arg Glu Leu Ser Thr Leu Leu Lys
275                     280                     285                     290

CAA GGT GCA GGG ACA AAG GGG TCA AAC AAG AAG AAG CTA CTC AGC ATG     1029
Gln Gly Ala Gly Thr Lys Gly Ser Asn Lys Lys Lys Leu Leu Ser Met
                295                     300                     305

TTA AGT GAC TAT TGG TAC TTA TCA TGC GGG CTT TTG TTT CCA AAG GCT     1077
Leu Ser Asp Tyr Trp Tyr Leu Ser Cys Gly Leu Leu Phe Pro Lys Ala
                310                     315                     320

GAA AGG TAC GAC AAA AGT ACA TGG CTC ACC AAG ACC CGG AAC ATA TGG     1125
Glu Arg Tyr Asp Lys Ser Thr Trp Leu Thr Lys Thr Arg Asn Ile Trp
        325                     330                     335

TCA GCT CCA TCC CCA ACA CAC CTC ATG ATC TCT ATG ATC ACC TGG CCC     1173
Ser Ala Pro Ser Pro Thr His Leu Met Ile Ser Met Ile Thr Trp Pro
    340                     345                     350

GTG ATG TCC AAC AGC CCA AAT AAC GTG TTG AAC ATT GAA GGG TGT CCA     1221
Val Met Ser Asn Ser Pro Asn Asn Val Leu Asn Ile Glu Gly Cys Pro
355                     360                     365                     370
```

| | | | | | | | | | | | | | | | | |
|---|---|---|---|---|---|---|---|---|---|---|---|---|---|---|---|---|
| TCA | CTC | TAC | AAA | TTC | AAC | CCG | TTC | AGA | GGA | GGG | TTG | AAC | AGG | ATC | GTC | 1269 |
| Ser | Leu | Tyr | Lys 375 | Phe | Asn | Pro | Phe | Arg 380 | Gly | Gly | Leu | Asn | Arg | Ile 385 | Val | |
| GAG | TGG | ATA | TTG | GCC | CCG | GAA | GAA | CCC | AAG | GCT | CTT | GTA | TAT | GCG | GAC | 1317 |
| Glu | Trp | Ile | Leu 390 | Ala | Pro | Glu | Glu | Pro 395 | Lys | Ala | Leu | Val | Tyr 400 | Ala | Asp | |
| AAC | ATA | TAC | ATT | GTC | CAC | TCA | AAC | ACG | TGG | TAC | TCA | ATT | GAC | CTA | GAG | 1365 |
| Asn | Ile | Tyr 405 | Ile | Val | His | Ser | Asn 410 | Thr | Trp | Tyr | Ser | Ile 415 | Asp | Leu | Glu | |
| AAG | GGT | GAG | GCA | AAC | TGC | ACT | CGC | CAA | CAC | ATG | CAA | GCC | GCA | ATG | TAC | 1413 |
| Lys | Gly | Glu 420 | Ala | Asn | Cys | Thr | Arg 425 | Gln | His | Met | Gln | Ala 430 | Ala | Met | Tyr | |
| TAC | ATA | CTC | ACC | AGA | GGG | TGG | TCA | GAC | AAC | GGC | GAC | CCA | ATG | TTC | AAT | 1461 |
| Tyr 435 | Ile | Leu | Thr | Arg | Gly 440 | Trp | Ser | Asp | Asn | Gly 445 | Asp | Pro | Met | Phe | Asn 450 | |
| CAA | ACA | TGG | GCC | ACC | TTT | GCC | ATG | AAC | ATT | GCC | CCT | GCT | CTA | GTG | GTG | 1509 |
| Gln | Thr | Trp | Ala | Thr 455 | Phe | Ala | Met | Asn | Ile 460 | Ala | Pro | Ala | Leu | Val 465 | Val | |
| GAC | TCA | TCG | TGC | CTG | ATA | ATG | AAC | CTG | CAA | ATT | AAG | ACC | TAT | GGT | CAA | 1557 |
| Asp | Ser | Ser | Cys 470 | Leu | Ile | Met | Asn | Leu 475 | Gln | Ile | Lys | Thr | Tyr 480 | Gly | Gln | |
| GGC | AGC | GGG | AAT | GCA | GCC | ACG | TTC | ATC | AAC | AAC | CAC | CTC | TTG | AGC | ACA | 1605 |
| Gly | Ser | Gly | Asn 485 | Ala | Ala | Thr | Phe | Ile 490 | Asn | Asn | His | Leu | Leu 495 | Ser | Thr | |
| CTA | GTG | CTT | GAC | CAG | TGG | AAC | CTG | ATG | AGA | CAG | CCC | AGA | CCA | GAC | AGC | 1653 |
| Leu | Val | Leu | Asp 500 | Gln | Trp | Asn | Leu | Met 505 | Arg | Gln | Pro | Arg | Pro 510 | Asp | Ser | |
| GAG | GAG | TTC | AAA | TCA | ATT | GAG | GAC | AAG | CTA | GGT | ATC | AAC | TTT | AAG | ATT | 1701 |
| Glu | Glu | Phe | Lys | Ser 515 | Ile | Glu | Asp | Lys | Leu 520 | Gly | Ile | Asn | Phe | Lys 525 | Ile 530 | |
| GAG | AGG | TCC | ATT | GAT | GAT | ATC | AGG | GGC | AAG | CTG | AGA | CAG | CTT | GTC | CTC | 1749 |
| Glu | Arg | Ser | Ile | Asp 535 | Asp | Ile | Arg | Gly | Lys 540 | Leu | Arg | Gln | Leu | Val 545 | Leu | |
| CTT | GCA | CAA | CCA | GGG | TAC | CTG | AGT | GGG | GGT | GTT | GAA | CCA | GAA | CAA | TCC | 1797 |
| Leu | Ala | Gln | Pro 550 | Gly | Tyr | Leu | Ser | Gly 555 | Gly | Val | Glu | Pro | Glu 560 | Gln | Ser | |
| AGC | CCA | ACT | GTT | GAG | CTT | GAC | CTA | CTA | GGG | TGG | TCA | GCT | ACA | TAC | AGC | 1845 |
| Ser | Pro | Thr 565 | Val | Glu | Leu | Asp | Leu 570 | Leu | Gly | Trp | Ser | Ala 575 | Thr | Tyr | Ser | |
| AAA | GAT | CTC | GGG | ATC | TAT | GTG | CCG | GTG | CTT | GAC | AAG | GAA | CGC | CTA | TTT | 1893 |
| Lys | Asp | Leu | Gly 580 | Ile | Tyr | Val | Pro | Val 585 | Leu | Asp | Lys | Glu | Arg 590 | Leu | Phe | |
| TGT | TCT | GCT | GCG | TAT | CCC | AAG | GGA | GTA | GAG | AAC | AAG | AGT | CTC | AAG | TCC | 1941 |
| Cys 595 | Ser | Ala | Ala | Tyr | Pro 600 | Lys | Gly | Val | Glu | Asn 605 | Lys | Ser | Leu | Lys | Ser 610 | |
| AAA | GTC | GGG | ATC | GAG | CAG | GCA | TAC | AAG | GTA | GTC | AGG | TAT | GAG | GCG | TTG | 1989 |
| Lys | Val | Gly | Ile | Glu 615 | Gln | Ala | Tyr | Lys | Val 620 | Val | Arg | Tyr | Glu | Ala 625 | Leu | |
| AGG | TTG | GTA | GGT | GGT | TGG | AAC | TAC | CCA | CTC | CTG | AAC | AAA | GCC | TGC | AAG | 2037 |
| Arg | Leu | Val | Gly 630 | Gly | Trp | Asn | Tyr | Pro 635 | Leu | Leu | Asn | Lys | Ala 640 | Cys | Lys | |
| AAT | AAC | GCA | GGC | GCC | GCT | CGG | CGG | CAT | CTG | GAG | GCC | AAG | GGG | TTC | CCA | 2085 |
| Asn | Asn | Ala 645 | Gly | Ala | Ala | Arg | Arg 650 | His | Leu | Glu | Ala | Lys 655 | Gly | Phe | Pro | |
| CTC | GAC | GAG | TTC | CTA | GCC | GAG | TGG | TCT | GAG | CTG | TCA | GAG | TTC | GGT | GAG | 2133 |
| Leu | Asp | Glu | Phe | Leu 660 | Ala | Glu | Trp | Ser | Glu 665 | Leu | Ser | Glu | Phe | Gly 670 | Glu | |
| GCC | TTC | GAA | GGC | TTC | AAT | ATC | AAG | CTG | ACC | GTA | ACA | TCT | GAG | AGC | CTA | 2181 |
| Ala | Phe | Glu | Gly 675 | Phe | Asn | Ile | Lys | Leu 680 | Thr | Val | Thr | Ser | Glu 685 | Ser | Leu 690 | |

```
GCC  GAA  CTG  AAC  AAG  CCA  GTA  CCC  CCC  AAG  CCC  CCA  AAT  GTC  AAC  AGA    2229
Ala  Glu  Leu  Asn  Lys  Pro  Val  Pro  Pro  Lys  Pro  Pro  Asn  Val  Asn  Arg
               695                      700                      705

CCA  GTC  AAC  ACT  GGG  GGA  CTC  AAG  GCA  GTC  AGC  AAC  GCC  CTC  AAG  ACC    2277
Pro  Val  Asn  Thr  Gly  Gly  Leu  Lys  Ala  Val  Ser  Asn  Ala  Leu  Lys  Thr
               710                      715                      720

GGT  CGG  TAC  AGG  AAC  GAA  GCC  GGA  CTG  AGT  GGT  CTC  GTC  CTT  CTA  GCC    2325
Gly  Arg  Tyr  Arg  Asn  Glu  Ala  Gly  Leu  Ser  Gly  Leu  Val  Leu  Leu  Ala
               725                      730                      735

ACA  GCA  AGA  AGC  CGT  CTG  CAA  GAT  GCA  GTT  AAG  GCC  AAG  GCA  GAA  GCC    2373
Thr  Ala  Arg  Ser  Arg  Leu  Gln  Asp  Ala  Val  Lys  Ala  Lys  Ala  Glu  Ala
               740                      745                      750

GAG  AAA  CTC  CAC  AAG  TCC  AAG  CCA  GAC  GAC  CCC  GAT  GCA  GAC  TGG  TTC    2421
Glu  Lys  Leu  His  Lys  Ser  Lys  Pro  Asp  Asp  Pro  Asp  Ala  Asp  Trp  Phe
755                 760                      765                      770

GAA  AGA  TCA  GAA  ACT  CTG  TCA  GAC  CTT  CTG  GAG  AAA  GCC  GAC  ATC  GCC    2469
Glu  Arg  Ser  Glu  Thr  Leu  Ser  Asp  Leu  Leu  Glu  Lys  Ala  Asp  Ile  Ala
                    775                      780                      785

AGC  AAG  GTC  GCC  CAC  TCA  GCA  CTC  GTG  GAA  ACA  AGC  GAC  GCC  CTT  GAA    2517
Ser  Lys  Val  Ala  His  Ser  Ala  Leu  Val  Glu  Thr  Ser  Asp  Ala  Leu  Glu
               790                      795                      800

GCA  GTT  CAG  TCG  ACT  TCC  GTG  TAC  ACC  CCC  AAG  TAC  CCA  GAA  GTC  AAG    2565
Ala  Val  Gln  Ser  Thr  Ser  Val  Tyr  Thr  Pro  Lys  Tyr  Pro  Glu  Val  Lys
               805                      810                      815

AAC  CCA  CAG  ACC  GCC  TCC  AAC  CCC  GTT  GTT  GGG  CTC  CAC  CTG  CCC  GCC    2613
Asn  Pro  Gln  Thr  Ala  Ser  Asn  Pro  Val  Val  Gly  Leu  His  Leu  Pro  Ala
820                 825                      830

AAG  AGA  GCC  ACC  GGT  GTC  CAG  GCC  GCT  CTT  CTC  GGA  GCA  GGA  ACG  AGC    2661
Lys  Arg  Ala  Thr  Gly  Val  Gln  Ala  Ala  Leu  Leu  Gly  Ala  Gly  Thr  Ser
835                 840                      845                      850

AGA  CCA  ATG  GGG  ATG  GAG  GCC  CCA  ACA  CGG  TCC  AAG  AAC  GCC  GTG  AAA    2709
Arg  Pro  Met  Gly  Met  Glu  Ala  Pro  Thr  Arg  Ser  Lys  Asn  Ala  Val  Lys
                    855                      860                      865

ATG  GCC  AAA  CGG  CGG  CAA  CGC  CAA  AAG  GAG  AGC  CGC  TAACAGCCAT             2755
Met  Ala  Lys  Arg  Arg  Gln  Arg  Gln  Lys  Glu  Ser  Arg
               870                      875

GATGGGAACC  ACTCAAGAAG  AGGACACTAA  TCCCAGACCC  CGTATCCCCG  GCCTTCGCCT    2815

GCGGGGGCCC  CC                                                            2827
```

( 2 ) INFORMATION FOR SEQ ID NO:26:

( i ) SEQUENCE CHARACTERISTICS:
        ( A ) LENGTH: 878 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met  Ser  Asp  Ile  Phe  Asn  Ser  Pro  Gln  Ala  Arg  Ser  Thr  Ile  Ser  Ala
1                   5                        10                       15

Ala  Phe  Gly  Ile  Lys  Pro  Thr  Ala  Gly  Gln  Asp  Val  Glu  Glu  Leu  Leu
               20                       25                       30

Ile  Pro  Lys  Val  Trp  Val  Pro  Pro  Glu  Asp  Pro  Leu  Ala  Ser  Pro  Ser
               35                       40                       45

Arg  Leu  Ala  Lys  Phe  Leu  Arg  Glu  Asn  Gly  Tyr  Lys  Val  Leu  Gln  Pro
          50                       55                       60

Arg  Ser  Leu  Pro  Glu  Asn  Glu  Glu  Tyr  Glu  Thr  Asp  Gln  Ile  Leu  Pro
65                  70                       75                       80
```

```
Asp Leu Ala Trp Met Arg Gln Ile Glu Gly Ala Val Leu Lys Pro Thr
             85                  90                  95
Leu Ser Leu Pro Ile Gly Asp Gln Glu Tyr Phe Pro Lys Tyr Tyr Pro
            100                 105                 110
Thr His Arg Pro Ser Lys Glu Lys Pro Asn Ala Tyr Pro Pro Asp Ile
            115                 120                 125
Ala Leu Leu Lys Gln Met Ile Tyr Leu Phe Leu Gln Val Pro Glu Ala
    130                 135                 140
Asn Glu Gly Leu Lys Asp Glu Val Thr Leu Leu Thr Gln Asn Ile Arg
145                 150                 155                 160
Asp Lys Ala Tyr Gly Ser Gly Thr Tyr Met Gly Gln Ala Asn Arg Leu
                165                 170                 175
Val Ala Met Lys Glu Val Ala Thr Gly Arg Asn Pro Asn Lys Asp Pro
            180                 185                 190
Leu Lys Leu Gly Tyr Thr Phe Glu Ser Ile Ala Gln Leu Leu Asp Ile
            195                 200                 205
Thr Leu Pro Val Gly Pro Pro Gly Glu Asp Asp Lys Pro Trp Val Pro
    210                 215                 220
Leu Thr Arg Val Pro Ser Arg Met Leu Val Leu Thr Gly Asp Val Asp
225                 230                 235                 240
Gly Asp Phe Glu Val Glu Asp Tyr Leu Pro Lys Ile Asn Leu Lys Ser
                245                 250                 255
Ser Ser Gly Leu Pro Tyr Val Gly Arg Thr Lys Gly Glu Thr Ile Gly
            260                 265                 270
Glu Met Ile Ala Ile Ser Asn Gln Phe Leu Arg Glu Leu Ser Thr Leu
            275                 280                 285
Leu Lys Gln Gly Ala Gly Thr Lys Gly Ser Asn Lys Lys Lys Leu Leu
    290                 295                 300
Ser Met Leu Ser Asp Tyr Trp Tyr Leu Ser Cys Gly Leu Leu Phe Pro
305                 310                 315                 320
Lys Ala Glu Arg Tyr Asp Lys Ser Thr Trp Leu Thr Lys Thr Arg Asn
                325                 330                 335
Ile Trp Ser Ala Pro Ser Pro Thr His Leu Met Ile Ser Met Ile Thr
            340                 345                 350
Trp Pro Val Met Ser Asn Ser Pro Asn Asn Val Leu Asn Ile Glu Gly
            355                 360                 365
Cys Pro Ser Leu Tyr Lys Phe Asn Pro Phe Arg Gly Gly Leu Asn Arg
    370                 375                 380
Ile Val Glu Trp Ile Leu Ala Pro Glu Glu Pro Lys Ala Leu Val Tyr
385                 390                 395                 400
Ala Asp Asn Ile Tyr Ile Val His Ser Asn Thr Trp Tyr Ser Ile Asp
                405                 410                 415
Leu Glu Lys Gly Glu Ala Asn Cys Thr Arg Gln His Met Gln Ala Ala
            420                 425                 430
Met Tyr Tyr Ile Leu Thr Arg Gly Trp Ser Asp Asn Gly Asp Pro Met
            435                 440                 445
Phe Asn Gln Thr Trp Ala Thr Phe Ala Met Asn Ile Ala Pro Ala Leu
    450                 455                 460
Val Val Asp Ser Ser Cys Leu Ile Met Asn Leu Gln Ile Lys Thr Tyr
465                 470                 475                 480
Gly Gln Gly Ser Gly Asn Ala Ala Thr Phe Ile Asn Asn His Leu Leu
                485                 490                 495
Ser Thr Leu Val Leu Asp Gln Trp Asn Leu Met Arg Gln Pro Arg Pro
            500                 505                 510
```

```
Asp  Ser  Glu  Glu  Phe  Lys  Ser  Ile  Glu  Asp  Lys  Leu  Gly  Ile  Asn  Phe
          515                      520                     525

Lys  Ile  Glu  Arg  Ser  Ile  Asp  Asp  Ile  Arg  Gly  Lys  Leu  Arg  Gln  Leu
     530                      535                     540

Val  Leu  Leu  Ala  Gln  Pro  Gly  Tyr  Leu  Ser  Gly  Val  Glu  Pro  Glu
545                      550                     555                          560

Gln  Ser  Ser  Pro  Thr  Val  Glu  Leu  Asp  Leu  Gly  Trp  Ser  Ala  Thr
                    565                     570                     575

Tyr  Ser  Lys  Asp  Leu  Gly  Ile  Tyr  Val  Pro  Val  Leu  Asp  Lys  Glu  Arg
               580                     585                     590

Leu  Phe  Cys  Ser  Ala  Ala  Tyr  Pro  Lys  Gly  Val  Glu  Asn  Lys  Ser  Leu
          595                      600                     605

Lys  Ser  Lys  Val  Gly  Ile  Glu  Gln  Ala  Tyr  Lys  Val  Val  Arg  Tyr  Glu
     610                      615                     620

Ala  Leu  Arg  Leu  Val  Gly  Gly  Trp  Asn  Tyr  Pro  Leu  Leu  Asn  Lys  Ala
625                      630                     635                          640

Cys  Lys  Asn  Asn  Ala  Gly  Ala  Ala  Arg  Arg  His  Leu  Glu  Ala  Lys  Gly
               645                     650                     655

Phe  Pro  Leu  Asp  Glu  Phe  Leu  Ala  Glu  Trp  Ser  Glu  Leu  Ser  Glu  Phe
               660                     665                     670

Gly  Glu  Ala  Phe  Glu  Gly  Phe  Asn  Ile  Lys  Leu  Thr  Val  Thr  Ser  Glu
          675                      680                     685

Ser  Leu  Ala  Glu  Leu  Asn  Lys  Pro  Val  Pro  Pro  Lys  Pro  Pro  Asn  Val
     690                      695                     700

Asn  Arg  Pro  Val  Asn  Thr  Gly  Gly  Leu  Lys  Ala  Val  Ser  Asn  Ala  Leu
705                      710                     715                          720

Lys  Thr  Gly  Arg  Tyr  Arg  Asn  Glu  Ala  Gly  Leu  Ser  Gly  Leu  Val  Leu
                    725                     730                     735

Leu  Ala  Thr  Ala  Arg  Ser  Arg  Leu  Gln  Asp  Ala  Val  Lys  Ala  Lys  Ala
               740                     745                     750

Glu  Ala  Glu  Lys  Leu  His  Lys  Ser  Lys  Pro  Asp  Asp  Pro  Asp  Ala  Asp
          755                      760                     765

Trp  Phe  Glu  Arg  Ser  Glu  Thr  Leu  Ser  Asp  Leu  Leu  Glu  Lys  Ala  Asp
770                      775                     780

Ile  Ala  Ser  Lys  Val  Ala  His  Ser  Ala  Leu  Val  Glu  Thr  Ser  Asp  Ala
785                      790                     795                          800

Leu  Glu  Ala  Val  Gln  Ser  Thr  Ser  Val  Tyr  Thr  Pro  Lys  Tyr  Pro  Glu
                    805                     810                     815

Val  Lys  Asn  Pro  Gln  Thr  Ala  Ser  Asn  Pro  Val  Val  Gly  Leu  His  Leu
               820                     825                     830

Pro  Ala  Lys  Arg  Ala  Thr  Gly  Val  Gln  Ala  Ala  Leu  Leu  Gly  Ala  Gly
          835                      840                     845

Thr  Ser  Arg  Pro  Met  Gly  Met  Glu  Ala  Pro  Thr  Arg  Ser  Lys  Asn  Ala
     850                      855                     860

Val  Lys  Met  Ala  Lys  Arg  Arg  Gln  Arg  Gln  Lys  Glu  Ser  Arg
865                      870                     875
```

( 2 ) INFORMATION FOR SEQ ID NO:27:

( i ) SEQUENCE CHARACTERISTICS:
        ( A ) LENGTH: 3261 base pairs
        ( B ) TYPE: nucleic acid
        ( C ) STRANDEDNESS: single
        ( D ) TOPOLOGY: circular ( i i ) MOLECULE TYPE: cDNA ( i x ) FEATURE:
    ( A ) NAME/KEY: CDS
    ( B ) LOCATION: 97..531

( x i ) SEQUENCE DESCRIPTION: SEQ ID NO:27:

```
GGATACGATC  GGTCTGACCC  CGGGGGAGTC  ACCCGGGGAC  AGGCCGTCAA  GGCCTTGTTC         60

CAGGATGGGA  CTCCTCCTTC  TACAACGCTA  TCATTG ATG GTT AGT AGA GAT CAG            114
                                           Met Val Ser Arg Asp Gln
                                               880

ACA AAC GAT CGC AGC GAT GAC AAA CCT GCA AGA TCA AAC CCA ACA GAT              162
Thr Asn Asp Arg Ser Asp Asp Lys Pro Ala Arg Ser Asn Pro Thr Asp
885             890                 895                 900

TGT TCC GTT CAT ACG GAG CCT TCT GAT GCC AAC AAC CGG ACC GGC GTC              210
Cys Ser Val His Thr Glu Pro Ser Asp Ala Asn Asn Arg Thr Gly Val
            905                 910                 915

CAT TCC GGA CGA CAC CCT GGA GAA GCA CAC TCT CAG GTC AGA GAC CTC              258
His Ser Gly Arg His Pro Gly Glu Ala His Ser Gln Val Arg Asp Leu
        920                 925                 930

GAC CTA CAA TTT GAC TGT GGG GGA CAC AGG GTC AGG GCT AAT TGT CTT              306
Asp Leu Gln Phe Asp Cys Gly Gly His Arg Val Arg Ala Asn Cys Leu
            935                 940                 945

TTT CCC TGG ATT CCC TGG CTC AAT TGT GGG TGC TCA CTA CAC ACT GCA              354
Phe Pro Trp Ile Pro Trp Leu Asn Cys Gly Cys Ser Leu His Thr Ala
950                 955                 960

GGG CAA TGG GAA CTA CAA GTT CGA TCA GAT GCT CCT GAC TGC CCA GAA              402
Gly Gln Trp Glu Leu Gln Val Arg Ser Asp Ala Pro Asp Cys Pro Glu
965                 970                 975                 980

CCT ACC GGC CAG TTA CAA CTA CTG CAG GCT AGT GAG TCG GAG TCT CAC              450
Pro Thr Gly Gln Leu Gln Leu Leu Gln Ala Ser Glu Ser Glu Ser His
            985                 990                 995

AGT GAG GTC AAG CAC ACT TCC TGG TGG CGT TTA TGC ACT AAA CGG CAC              498
Ser Glu Val Lys His Thr Ser Trp Trp Arg Leu Cys Thr Lys Arg His
        1000                1005                1010

CAT AAA CGC CGT GAC CTT CCA AGG AAG CCT GAG TGAACTGACA GATGTTAGCT            551
His Lys Arg Arg Asp Leu Pro Arg Lys Pro Glu
        1015                1020

ACAATGGGTT  GATGTCTGCA  ACAGCCAACA  TCAACGACAA  AATTGGGAAC  GTCCTAGTAG       611

GGGAAGGGGT  CACCGTCCTC  AGCTTACCCA  CATCATATGA  TCTTGGGTAT  GTGAGGCTTG       671

GTGACCCCAT  TCCCGCAATA  GGGCTTGACC  CAAAAATGGT  AGCCACATGT  GACAGCAGTG       731

ACAGGCCCAG  AGTCTACACC  ATAACTGCAG  CCGATGATTA  CCAATTCTCA  TCACAGTACC       791

AACCAGGTGG  GGTAACAATC  ACACTGTTCT  CAGCCAACAT  TGATGCCATC  ACAAGCCTCA       851

GCGTTGGGGG  AGAGCTCGTG  TTTCAAACAA  GCGTCCACGG  CCTTGTACTG  GGCGCCACCA       911

TCTACCTCAT  AGGCTTTGAT  GGGACAACGG  TAATCACCAG  GGCTGTGGCC  GCAAACAATG       971

GGCTGACGAC  CGGCACCGAC  AACCTTATGC  CATTCAATCT  TGTGATTCCA  ACAAACGAGA      1031

TAACCCAGCC  AATCACATCC  ATCAAACTGG  AGATAGTGAC  CTCCAAAAGT  GGTGGTCAGG      1091

CAGGGGATCA  GATGTCATGG  TCGGCAAGAG  GGAGCCTAGC  AGTGACGATC  CATGGTGGCA      1151

ACTATCCAGG  GGCCCTCCGT  CCCGTCACGC  TAGTGGCCTA  CGAAAGAGTG  GCAACAGGAT      1211

CCGTCGTTAC  GGTCGCTGGG  GTGAGCAACT  TCGAGCTGAT  CCCAAATCCT  GAACTAGCAA      1271

AGAACCTGGT  TACAGAATAC  GGCCGATTTG  ACCCAGGAGC  CATGAACTAC  ACAAAATTGA      1331

TACTGAGTGA  GAGGGACCGT  CTTGGCATCA  AGACCGTCTG  GCCAACAAGG  GAGTACACTG      1391

ACTTTCGTGA  ATACTTCATG  GAGGTGGCCG  ACCTCAACTC  TCCCCTGAAG  ATTGCAGGAG      1451

CATTCGGCTT  CAAAGACATA  ATCCGGGCCA  TAAGGAGGAT  AGCTGTGCCG  GTGGTCTCCA      1511
```

| | | | | | |
|---|---|---|---|---|---|
| CATTGTTCCC | ACCTGCCGCT | CCCCTAGCCC | ATGCAATTGG | GGAAGGTGTA | GACTACCTGC | 1571
| TGGGCGATGA | GGCACAGGCT | GCTTCAGGAA | CTGCTCGAGC | CGCGTCAGGA | AAAGCAAGAG | 1631
| CTGCCTCAGG | CCGCATAAGG | CAGCTGACTC | TCGCCGCCGA | CAAGGGGTAC | GAGGTAGTCG | 1691
| CGAATCTATT | CCAGGTGCCC | CAGAATCCCG | TAGTCGACGG | GATTCTTGCT | TCACCTGGGG | 1751
| TACTCCGCGG | TGCACACAAC | CTCGACTGCG | TGTTAAGAGA | GGGTGCCACG | CTATTCCCTG | 1811
| TGGTTATTAC | GACAGTGGAA | GACGCCATGA | CACCCAAAGC | ATTGAACAGC | AAAATGTTTG | 1871
| CTGTCATTGA | AGGCGTGCGA | GAAGACCTCC | AACCTCCATC | TCAAAGAGGA | TCCTTCATAC | 1931
| GAACTCTCTC | TGGACACAGA | GTCTATGGAT | ATGCTCCAGA | TGGGGTACTT | CCACTGGAGA | 1991
| CTGGGAGAGA | CTACACCGTT | GTCCCAATAG | ATGATGTCTG | GGACGACAGC | ATTATGCTGT | 2051
| CCAAAGATCC | CATACCTCCT | ATTGTGGGAA | ACAGTGGAAA | TCTAGCCATA | GCTTACATGG | 2111
| ATGTGTTTCG | ACCCAAAGTC | CCAATCCATG | TGGCTATGAC | GGGAGCCCTC | AATGCTTGTG | 2171
| GCGAGATTGA | GAAAGTAAGC | TTTAGAAGCA | CCAAGCTCGC | CACTGCACAC | CGACTTGGCC | 2231
| TTAGGTTGGC | TGGTCCCGGA | GCATTCGATG | TAAACACCGG | GCCCAACTGG | CAACGTTCA | 2291
| TCAAACGTTT | CCCTCACAAT | CCACGCGACT | GGGACAGGCT | CCCCTACCTC | AACCTACCAT | 2351
| ACCTTCCACC | CAATGCAGGA | CGCCAGTACC | ACCTTGCCAT | GGCTGCATCA | GAGTTCAAAG | 2411
| AGACCCCCGA | ACTCGAGAGT | GCCGTCAGAG | CAATGGAAGC | AGCAGCCAAC | GTGGACCCAC | 2471
| TATTCCAATC | TGCACTCAGT | GTGTTCATGT | GGCTGGAAGA | GAATGGGATT | GTGACTGACA | 2531
| TGGCCAACTT | CGCACTCAGC | GACCCGAACG | CCCATCGGAT | GCGAAATTTT | CTTGCAAACG | 2591
| CACCACAAGC | AGGCAGCAAG | TCGCAAAGGG | CCAAGTACGG | GACAGCAGGC | TACGGAGTGG | 2651
| AGGCTCGGGG | CCCCACACCA | GAGGAAGCAC | AGAGGGAAAA | AGACACACGG | ATCTCAAAGA | 2711
| AGATGGAGAC | CATGGGCATC | TACTTTGCAA | CACCAGAATG | GGTAGCACTC | AATGGGCACC | 2771
| GAGGGCCAAG | CCCCGGCCAG | CTAAAGTACT | GGCAGAACAC | ACGAGAAATA | CCGGACCCAA | 2831
| ACGAGGACTA | TCTAGACTAC | GTGCATGCAG | AGAAGAGCCG | GTTGGCATCA | GAAGAACAAA | 2891
| TCCTAAGGGC | AGCTACGTCG | ATCTACGGGG | CTCCAGGACA | GGCAGAGCCA | CCCCAAGCTT | 2951
| TCATAGACGA | AGTTGCCAAA | GTCTATGAAA | TCAACCATGG | ACGTGGCCCA | AACCAAGAAC | 3011
| AGATGAAAGA | TCTGCTCTTG | ACTGCGATGG | AGATGAAGCA | TCGCAATCCC | AGGCGGGCTC | 3071
| TACCAAAGCC | CAAGCCAAAA | CCCAATGCTC | AACACAGAG | ACCCCCTGGT | CGGCTGGGCC | 3131
| GCTGGATCAG | GACCGTCTCT | GATGAGGACC | TTGAGTGAGG | CTCCTGGGAG | TCTCCCGACA | 3191
| CCACCCGCGC | AGGTGTGGAC | ACCAATTCGG | CCTTACAACA | TCCCAAATTG | GATCCGTTCG | 3251
| CGGGTCCCCT | | | | | | 3261

( 2 ) INFORMATION FOR SEQ ID NO:28:

( i ) SEQUENCE CHARACTERISTICS:
        ( A ) LENGTH: 145 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| Met | Val | Ser | Arg | Asp | Gln | Thr | Asn | Asp | Arg | Ser | Asp | Asp | Lys | Pro | Ala |
|---|---|---|---|---|---|---|---|---|---|---|---|---|---|---|---|
| 1 | | | | 5 | | | | | 10 | | | | | 15 | |

| Arg | Ser | Asn | Pro | Thr | Asp | Cys | Ser | Val | His | Thr | Glu | Pro | Ser | Asp | Ala |
|---|---|---|---|---|---|---|---|---|---|---|---|---|---|---|---|
| | | | | 20 | | | | | 25 | | | | | 30 | |

| Asn | Asn | Arg | Thr | Gly | Val | His | Ser | Gly | Arg | His | Pro | Gly | Glu | Ala | His |

|  | 3 5 |  |  |  | 4 0 |  |  |  |  | 4 5 |  |  |  |  |
|---|---|---|---|---|---|---|---|---|---|---|---|---|---|---|
| Ser | Gln | Val | Arg | Asp | Leu | Asp | Leu | Gln | Phe | Asp | Cys | Gly | Gly | His | Arg |
|  | 50 |  |  |  | 55 |  |  |  |  | 60 |  |  |  |  |
| Val | Arg | Ala | Asn | Cys | Leu | Phe | Pro | Trp | Ile | Pro | Trp | Leu | Asn | Cys | Gly |
| 65 |  |  |  | 70 |  |  |  |  | 75 |  |  |  |  | 80 |
| Cys | Ser | Leu | His | Thr | Ala | Gly | Gln | Trp | Glu | Leu | Gln | Val | Arg | Ser | Asp |
|  |  |  |  | 85 |  |  |  |  | 90 |  |  |  |  | 95 |
| Ala | Pro | Asp | Cys | Pro | Glu | Pro | Thr | Gly | Gln | Leu | Gln | Leu | Leu | Gln | Ala |
|  |  |  | 100 |  |  |  |  | 105 |  |  |  |  | 110 |
| Ser | Glu | Ser | Glu | Ser | His | Ser | Glu | Val | Lys | His | Thr | Ser | Trp | Trp | Arg |
|  |  | 115 |  |  |  |  | 120 |  |  |  |  | 125 |  |  |
| Leu | Cys | Thr | Lys | Arg | His | His | Lys | Arg | Arg | Asp | Leu | Pro | Arg | Lys | Pro |
|  | 130 |  |  |  |  | 135 |  |  |  |  | 140 |  |  |  |
| Glu |  |  |  |  |  |  |  |  |  |  |  |  |  |  |  |
| 145 |  |  |  |  |  |  |  |  |  |  |  |  |  |  |  |

( 2 ) INFORMATION FOR SEQ ID NO:29:

( i ) SEQUENCE CHARACTERISTICS:
        ( A ) LENGTH: 3261 base pairs
        ( B ) TYPE: nucleic acid
        ( C ) STRANDEDNESS: single
        ( D ) TOPOLOGY: circular ( i i ) MOLECULE TYPE: cDNA ( i x ) FEATURE:
        ( A ) NAME/KEY: CDS
        ( B ) LOCATION: 131..3166

( x i ) SEQUENCE DESCRIPTION: SEQ ID NO:29:

```
GGATACGATC  GGTCTGACCC  CGGGGGAGTC  ACCCGGGGAC  AGGCCGTCAA  GGCCTTGTTC        60

CAGGATGGGA  CTCCTCCTTC  TACAACGCTA  TCATTGATGG  TTAGTAGAGA  TCAGACAAAC       120

GATCGCAGCG ATG ACA AAC CTG CAA GAT CAA ACC CAA CAG ATT GTT CCG              169
           Met Thr Asn Leu Gln Asp Gln Thr Gln Gln Ile Val Pro
                               150                 155

TTC ATA CGG AGC CTT CTG ATG CCA ACA ACC GGA CCG GCG TCC ATT CCG             217
Phe Ile Arg Ser Leu Leu Met Pro Thr Thr Gly Pro Ala Ser Ile Pro
160                     165                 170

GAC GAC ACC CTG GAG AAG CAC ACT CTC AGG TCA GAG ACC TCG ACC TAC             265
Asp Asp Thr Leu Glu Lys His Thr Leu Arg Ser Glu Thr Ser Thr Tyr
175                     180                 185                 190

AAT TTG ACT GTG GGG GAC ACA GGG TCA GGG CTA ATT GTC TTT TTC CCT             313
Asn Leu Thr Val Gly Asp Thr Gly Ser Gly Leu Ile Val Phe Phe Pro
                    195                 200                 205

GGA TTC CCT GGC TCA ATT GTG GGT GCT CAC TAC ACA CTG CAG GGC AAT             361
Gly Phe Pro Gly Ser Ile Val Gly Ala His Tyr Thr Leu Gln Gly Asn
                210                 215                 220

GGG AAC TAC AAG TTC GAT CAG ATG CTC CTG ACT GCC CAG AAC CTA CCG             409
Gly Asn Tyr Lys Phe Asp Gln Met Leu Leu Thr Ala Gln Asn Leu Pro
            225                 230                 235

GCC AGT TAC AAC TAC TGC AGG CTA GTG AGT CGG AGT CTC ACA GTG AGG             457
Ala Ser Tyr Asn Tyr Cys Arg Leu Val Ser Arg Ser Leu Thr Val Arg
    240                 245                 250

TCA AGC ACA CTT CCT GGT GGC GTT TAT GCA CTA AAC GGC ACC ATA AAC             505
Ser Ser Thr Leu Pro Gly Gly Val Tyr Ala Leu Asn Gly Thr Ile Asn
255                 260                 265                 270

GCC GTG ACC TTC CAA GGA AGC CTG AGT GAA CTG ACA GAT GTT AGC TAC             553
Ala Val Thr Phe Gln Gly Ser Leu Ser Glu Leu Thr Asp Val Ser Tyr
                275                 280                 285
```

```
AAT  GGG  TTG  ATG  TCT  GCA  ACA  GCC  AAC  ATC  AAC  GAC  AAA  ATT  GGG  AAC    601
Asn  Gly  Leu  Met  Ser  Ala  Thr  Ala  Asn  Ile  Asn  Asp  Lys  Ile  Gly  Asn
               290                 295                 300

GTC  CTA  GTA  GGG  GAA  GGG  GTC  ACC  GTC  CTC  AGC  TTA  CCC  ACA  TCA  TAT    649
Val  Leu  Val  Gly  Glu  Gly  Val  Thr  Val  Leu  Ser  Leu  Pro  Thr  Ser  Tyr
          305                 310                 315

GAT  CTT  GGG  TAT  GTG  AGG  CTT  GGT  GAC  CCC  ATT  CCC  GCA  ATA  GGG  CTT    697
Asp  Leu  Gly  Tyr  Val  Arg  Leu  Gly  Asp  Pro  Ile  Pro  Ala  Ile  Gly  Leu
     320                 325                 330

GAC  CCA  AAA  ATG  GTA  GCC  ACA  TGT  GAC  AGC  AGT  GAC  AGG  CCC  AGA  GTC    745
Asp  Pro  Lys  Met  Val  Ala  Thr  Cys  Asp  Ser  Ser  Asp  Arg  Pro  Arg  Val
335                      340                 345                      350

TAC  ACC  ATA  ACT  GCA  GCC  GAT  GAT  TAC  CAA  TTC  TCA  TCA  CAG  TAC  CAA    793
Tyr  Thr  Ile  Thr  Ala  Ala  Asp  Asp  Tyr  Gln  Phe  Ser  Ser  Gln  Tyr  Gln
                    355                 360                 365

CCA  GGT  GGG  GTA  ACA  ATC  ACA  CTG  TTC  TCA  GCC  AAC  ATT  GAT  GCC  ATC    841
Pro  Gly  Gly  Val  Thr  Ile  Thr  Leu  Phe  Ser  Ala  Asn  Ile  Asp  Ala  Ile
               370                 375                 380

ACA  AGC  CTC  AGC  GTT  GGG  GGA  GAG  CTC  GTG  TTT  CAA  ACA  AGC  GTC  CAC    889
Thr  Ser  Leu  Ser  Val  Gly  Gly  Glu  Leu  Val  Phe  Gln  Thr  Ser  Val  His
          385                 390                 395

GGC  CTT  GTA  CTG  GGC  GCC  ACC  ATC  TAC  CTC  ATA  GGC  TTT  GAT  GGG  ACA    937
Gly  Leu  Val  Leu  Gly  Ala  Thr  Ile  Tyr  Leu  Ile  Gly  Phe  Asp  Gly  Thr
     400                 405                 410

ACG  GTA  ATC  ACC  AGG  GCT  GTG  GCC  GCA  AAC  AAT  GGG  CTG  ACG  ACC  GGC    985
Thr  Val  Ile  Thr  Arg  Ala  Val  Ala  Ala  Asn  Asn  Gly  Leu  Thr  Thr  Gly
415                      420                 425                      430

ACC  GAC  AAC  CTT  ATG  CCA  TTC  AAT  CTT  GTG  ATT  CCA  ACA  AAC  GAG  ATA   1033
Thr  Asp  Asn  Leu  Met  Pro  Phe  Asn  Leu  Val  Ile  Pro  Thr  Asn  Glu  Ile
                    435                 440                 445

ACC  CAG  CCA  ATC  ACA  TCC  ATC  AAA  CTG  GAG  ATA  GTG  ACC  TCC  AAA  AGT   1081
Thr  Gln  Pro  Ile  Thr  Ser  Ile  Lys  Leu  Glu  Ile  Val  Thr  Ser  Lys  Ser
               450                 455                 460

GGT  GGT  CAG  GCA  GGG  GAT  CAG  ATG  TCA  TGG  TCG  GCA  AGA  GGG  AGC  CTA   1129
Gly  Gly  Gln  Ala  Gly  Asp  Gln  Met  Ser  Trp  Ser  Ala  Arg  Gly  Ser  Leu
          465                 470                 475

GCA  GTG  ACG  ATC  CAT  GGT  GGC  AAC  TAT  CCA  GGG  GCC  CTC  CGT  CCC  GTC   1177
Ala  Val  Thr  Ile  His  Gly  Gly  Asn  Tyr  Pro  Gly  Ala  Leu  Arg  Pro  Val
     480                 485                 490

ACG  CTA  GTG  GCC  TAC  GAA  AGA  GTG  GCA  ACA  GGA  TCC  GTC  GTT  ACG  GTC   1225
Thr  Leu  Val  Ala  Tyr  Glu  Arg  Val  Ala  Thr  Gly  Ser  Val  Val  Thr  Val
495                      500                 505                      510

GCT  GGG  GTG  AGC  AAC  TTC  GAG  CTG  ATC  CCA  AAT  CCT  GAA  CTA  GCA  AAG   1273
Ala  Gly  Val  Ser  Asn  Phe  Glu  Leu  Ile  Pro  Asn  Pro  Glu  Leu  Ala  Lys
                    515                 520                 525

AAC  CTG  GTT  ACA  GAA  TAC  GGC  CGA  TTT  GAC  CCA  GGA  GCC  ATG  AAC  TAC   1321
Asn  Leu  Val  Thr  Glu  Tyr  Gly  Arg  Phe  Asp  Pro  Gly  Ala  Met  Asn  Tyr
               530                 535                 540

ACA  AAA  TTG  ATA  CTG  AGT  GAG  AGG  GAC  CGT  CTT  GGC  ATC  AAG  ACC  GTC   1369
Thr  Lys  Leu  Ile  Leu  Ser  Glu  Arg  Asp  Arg  Leu  Gly  Ile  Lys  Thr  Val
          545                 550                 555

TGG  CCA  ACA  AGG  GAG  TAC  ACT  GAC  TTT  CGT  GAA  TAC  TTC  ATG  GAG  GTG   1417
Trp  Pro  Thr  Arg  Glu  Tyr  Thr  Asp  Phe  Arg  Glu  Tyr  Phe  Met  Glu  Val
     560                 565                 570

GCC  GAC  CTC  AAC  TCT  CCC  CTG  AAG  ATT  GCA  GGA  GCA  TTC  GGC  TTC  AAA   1465
Ala  Asp  Leu  Asn  Ser  Pro  Leu  Lys  Ile  Ala  Gly  Ala  Phe  Gly  Phe  Lys
575                      580                 585                      590

GAC  ATA  ATC  CGG  GCC  ATA  AGG  AGG  ATA  GCT  GTG  CCG  GTG  GTC  TCC  ACA   1513
Asp  Ile  Ile  Arg  Ala  Ile  Arg  Arg  Ile  Ala  Val  Pro  Val  Val  Ser  Thr
                    595                 600                 605
```

| | | | | | | | | | | | | | | | |
|---|---|---|---|---|---|---|---|---|---|---|---|---|---|---|---|
| TTG | TTC | CCA | CCT | GCC | GCT | CCC | CTA | GCC | CAT | GCA | ATT | GGG | GAA | GGT | GTA | 1561
| Leu | Phe | Pro | Pro | Ala | Ala | Pro | Leu | Ala | His | Ala | Ile | Gly | Glu | Gly | Val |
| | | 610 | | | | | 615 | | | | | 620 | | | |
| GAC | TAC | CTG | CTG | GGC | GAT | GAG | GCA | CAG | GCT | GCT | TCA | GGA | ACT | GCT | CGA | 1609
| Asp | Tyr | Leu | Leu | Gly | Asp | Glu | Ala | Gln | Ala | Ala | Ser | Gly | Thr | Ala | Arg |
| | | 625 | | | | 630 | | | | | 635 | | | | |
| GCC | GCG | TCA | GGA | AAA | GCA | AGA | GCT | GCC | TCA | GGC | CGC | ATA | AGG | CAG | CTG | 1657
| Ala | Ala | Ser | Gly | Lys | Ala | Arg | Ala | Ala | Ser | Gly | Arg | Ile | Arg | Gln | Leu |
| 640 | | | | | 645 | | | | | 650 | | | | | |
| ACT | CTC | GCC | GCC | GAC | AAG | GGG | TAC | GAG | GTA | GTC | GCG | AAT | CTA | TTC | CAG | 1705
| Thr | Leu | Ala | Ala | Asp | Lys | Gly | Tyr | Glu | Val | Val | Ala | Asn | Leu | Phe | Gln |
| 655 | | | | | 660 | | | | | 665 | | | | | 670 |
| GTG | CCC | CAG | AAT | CCC | GTA | GTC | GAC | GGG | ATT | CTT | GCT | TCA | CCT | GGG | GTA | 1753
| Val | Pro | Gln | Asn | Pro | Val | Val | Asp | Gly | Ile | Leu | Ala | Ser | Pro | Gly | Val |
| | | | | 675 | | | | | 680 | | | | | 685 | |
| CTC | CGC | GGT | GCA | CAC | AAC | CTC | GAC | TGC | GTG | TTA | AGA | GAG | GGT | GCC | ACG | 1801
| Leu | Arg | Gly | Ala | His | Asn | Leu | Asp | Cys | Val | Leu | Arg | Glu | Gly | Ala | Thr |
| | | | | 690 | | | | 695 | | | | | 700 | | |
| CTA | TTC | CCT | GTG | GTT | ATT | ACG | ACA | GTG | GAA | GAC | GCC | ATG | ACA | CCC | AAA | 1849
| Leu | Phe | Pro | Val | Val | Ile | Thr | Thr | Val | Glu | Asp | Ala | Met | Thr | Pro | Lys |
| | | 705 | | | | | 710 | | | | | 715 | | | |
| GCA | TTG | AAC | AGC | AAA | ATG | TTT | GCT | GTC | ATT | GAA | GGC | GTG | CGA | GAA | GAC | 1897
| Ala | Leu | Asn | Ser | Lys | Met | Phe | Ala | Val | Ile | Glu | Gly | Val | Arg | Glu | Asp |
| 720 | | | | | 725 | | | | | 730 | | | | | |
| CTC | CAA | CCT | CCA | TCT | CAA | AGA | GGA | TCC | TTC | ATA | CGA | ACT | CTC | TCT | GGA | 1945
| Leu | Gln | Pro | Pro | Ser | Gln | Arg | Gly | Ser | Phe | Ile | Arg | Thr | Leu | Ser | Gly |
| 735 | | | | | 740 | | | | | 745 | | | | | 750 |
| CAC | AGA | GTC | TAT | GGA | TAT | GCT | CCA | GAT | GGG | GTA | CTT | CCA | CTG | GAG | ACT | 1993
| His | Arg | Val | Tyr | Gly | Tyr | Ala | Pro | Asp | Gly | Val | Leu | Pro | Leu | Glu | Thr |
| | | | | 755 | | | | | 760 | | | | | 765 | |
| GGG | AGA | GAC | TAC | ACC | GTT | GTC | CCA | ATA | GAT | GAT | GTC | TGG | GAC | GAC | AGC | 2041
| Gly | Arg | Asp | Tyr | Thr | Val | Val | Pro | Ile | Asp | Asp | Val | Trp | Asp | Asp | Ser |
| | | | 770 | | | | | 775 | | | | | 780 | | |
| ATT | ATG | CTG | TCC | AAA | GAT | CCC | ATA | CCT | CCT | ATT | GTG | GGA | AAC | AGT | GGA | 2089
| Ile | Met | Leu | Ser | Lys | Asp | Pro | Ile | Pro | Pro | Ile | Val | Gly | Asn | Ser | Gly |
| | | 785 | | | | | 790 | | | | | 795 | | | |
| AAT | CTA | GCC | ATA | GCT | TAC | ATG | GAT | GTG | TTT | CGA | CCC | AAA | GTC | CCA | ATC | 2137
| Asn | Leu | Ala | Ile | Ala | Tyr | Met | Asp | Val | Phe | Arg | Pro | Lys | Val | Pro | Ile |
| 800 | | | | | 805 | | | | | 810 | | | | | |
| CAT | GTG | GCT | ATG | ACG | GGA | GCC | CTC | AAT | GCT | TGT | GGC | GAG | ATT | GAG | AAA | 2185
| His | Val | Ala | Met | Thr | Gly | Ala | Leu | Asn | Ala | Cys | Gly | Glu | Ile | Glu | Lys |
| 815 | | | | | 820 | | | | | 825 | | | | | 830 |
| GTA | AGC | TTT | AGA | AGC | ACC | AAG | CTC | GCC | ACT | GCA | CAC | CGA | CTT | GGC | CTT | 2233
| Val | Ser | Phe | Arg | Ser | Thr | Lys | Leu | Ala | Thr | Ala | His | Arg | Leu | Gly | Leu |
| | | | | 835 | | | | | 840 | | | | | 845 | |
| AGG | TTG | GCT | GGT | CCC | GGA | GCA | TTC | GAT | GTA | AAC | ACC | GGG | CCC | AAC | TGG | 2281
| Arg | Leu | Ala | Gly | Pro | Gly | Ala | Phe | Asp | Val | Asn | Thr | Gly | Pro | Asn | Trp |
| | | | 850 | | | | | 855 | | | | | 860 | | |
| GCA | ACG | TTC | ATC | AAA | CGT | TTC | CCT | CAC | AAT | CCA | CGC | GAC | TGG | GAC | AGG | 2329
| Ala | Thr | Phe | Ile | Lys | Arg | Phe | Pro | His | Asn | Pro | Arg | Asp | Trp | Asp | Arg |
| | | 865 | | | | | 870 | | | | | 875 | | | |
| CTC | CCC | TAC | CTC | AAC | CTA | CCA | TAC | CTT | CCA | CCC | AAT | GCA | GGA | CGC | CAG | 2377
| Leu | Pro | Tyr | Leu | Asn | Leu | Pro | Tyr | Leu | Pro | Pro | Asn | Ala | Gly | Arg | Gln |
| 880 | | | | | 885 | | | | | 890 | | | | | |
| TAC | CAC | CTT | GCC | ATG | GCT | GCA | TCA | GAG | TTC | AAA | GAG | ACC | CCC | GAA | CTC | 2425
| Tyr | His | Leu | Ala | Met | Ala | Ala | Ser | Glu | Phe | Lys | Glu | Thr | Pro | Glu | Leu |
| 895 | | | | | 900 | | | | | 905 | | | | | 910 |
| GAG | AGT | GCC | GTC | AGA | GCA | ATG | GAA | GCA | GCA | GCC | AAC | GTG | GAC | CCA | CTA | 2473
| Glu | Ser | Ala | Val | Arg | Ala | Met | Glu | Ala | Ala | Ala | Asn | Val | Asp | Pro | Leu |
| | | | | 915 | | | | | 920 | | | | | 925 | |

| | | | | | | | | | | | | | | | | |
|---|---|---|---|---|---|---|---|---|---|---|---|---|---|---|---|---|
| TTC | CAA | TCT | GCA | CTC | AGT | GTG | TTC | ATG | TGG | CTG | GAA | GAG | AAT | GGG | ATT | 2521 |
| Phe | Gln | Ser | Ala | Leu | Ser | Val | Phe | Met | Trp | Leu | Glu | Glu | Asn | Gly | Ile | |
| | | | 930 | | | | | 935 | | | | | | 940 | | |
| GTG | ACT | GAC | ATG | GCC | AAC | TTC | GCA | CTC | AGC | GAC | CCG | AAC | GCC | CAT | CGG | 2569 |
| Val | Thr | Asp | Met | Ala | Asn | Phe | Ala | Leu | Ser | Asp | Pro | Asn | Ala | His | Arg | |
| | | 945 | | | | | 950 | | | | | 955 | | | | |
| ATG | CGA | AAT | TTT | CTT | GCA | AAC | GCA | CCA | CAA | GCA | GGC | AGC | AAG | TCG | CAA | 2617 |
| Met | Arg | Asn | Phe | Leu | Ala | Asn | Ala | Pro | Gln | Ala | Gly | Ser | Lys | Ser | Gln | |
| | 960 | | | | | 965 | | | | | 970 | | | | | |
| AGG | GCC | AAG | TAC | GGG | ACA | GCA | GGC | TAC | GGA | GTG | GAG | GCT | CGG | GGC | CCC | 2665 |
| Arg | Ala | Lys | Tyr | Gly | Thr | Ala | Gly | Tyr | Gly | Val | Glu | Ala | Arg | Gly | Pro | |
| 975 | | | | | 980 | | | | | 985 | | | | | 990 | |
| ACA | CCA | GAG | GAA | GCA | CAG | AGG | GAA | AAA | GAC | ACA | CGG | ATC | TCA | AAG | AAG | 2713 |
| Thr | Pro | Glu | Glu | Ala | Gln | Arg | Glu | Lys | Asp | Thr | Arg | Ile | Ser | Lys | Lys | |
| | | | | 995 | | | | | 1000 | | | | | 1005 | | |
| ATG | GAG | ACC | ATG | GGC | ATC | TAC | TTT | GCA | ACA | CCA | GAA | TGG | GTA | GCA | CTC | 2761 |
| Met | Glu | Thr | Met | Gly | Ile | Tyr | Phe | Ala | Thr | Pro | Glu | Trp | Val | Ala | Leu | |
| | | | 1010 | | | | | 1015 | | | | | 1020 | | | |
| AAT | GGG | CAC | CGA | GGG | CCA | AGC | CCC | GGC | CAG | CTA | AAG | TAC | TGG | CAG | AAC | 2809 |
| Asn | Gly | His | Arg | Gly | Pro | Ser | Pro | Gly | Gln | Leu | Lys | Tyr | Trp | Gln | Asn | |
| | | | 1025 | | | | | 1030 | | | | | 1035 | | | |
| ACA | CGA | GAA | ATA | CCG | GAC | CCA | AAC | GAG | GAC | TAT | CTA | GAC | TAC | GTG | CAT | 2857 |
| Thr | Arg | Glu | Ile | Pro | Asp | Pro | Asn | Glu | Asp | Tyr | Leu | Asp | Tyr | Val | His | |
| | | | 1040 | | | | | 1045 | | | | | 1050 | | | |
| GCA | GAG | AAG | AGC | CGG | TTG | GCA | TCA | GAA | GAA | CAA | ATC | CTA | AGG | GCA | GCT | 2905 |
| Ala | Glu | Lys | Ser | Arg | Leu | Ala | Ser | Glu | Glu | Gln | Ile | Leu | Arg | Ala | Ala | |
| 1055 | | | | | 1060 | | | | | 1065 | | | | | 1070 | |
| ACG | TCG | ATC | TAC | GGG | GCT | CCA | GGA | CAG | GCA | GAG | CCA | CCC | CAA | GCT | TTC | 2953 |
| Thr | Ser | Ile | Tyr | Gly | Ala | Pro | Gly | Gln | Ala | Glu | Pro | Pro | Gln | Ala | Phe | |
| | | | | 1075 | | | | | 1080 | | | | | 1085 | | |
| ATA | GAC | GAA | GTT | GCC | AAA | GTC | TAT | GAA | ATC | AAC | CAT | GGA | CGT | GGC | CCA | 3001 |
| Ile | Asp | Glu | Val | Ala | Lys | Val | Tyr | Glu | Ile | Asn | His | Gly | Arg | Gly | Pro | |
| | | | | 1090 | | | | | 1095 | | | | | 1100 | | |
| AAC | CAA | GAA | CAG | ATG | AAA | GAT | CTG | CTC | TTG | ACT | GCG | ATG | GAG | ATG | AAG | 3049 |
| Asn | Gln | Glu | Gln | Met | Lys | Asp | Leu | Leu | Leu | Thr | Ala | Met | Glu | Met | Lys | |
| | | | 1105 | | | | | 1110 | | | | | 1115 | | | |
| CAT | CGC | AAT | CCC | AGG | CGG | GCT | CTA | CCA | AAG | CCC | AAG | CCA | AAA | CCC | AAT | 3097 |
| His | Arg | Asn | Pro | Arg | Arg | Ala | Leu | Pro | Lys | Pro | Lys | Pro | Lys | Pro | Asn | |
| | | | 1120 | | | | | 1125 | | | | | 1130 | | | |
| GCT | CCA | ACA | CAG | AGA | CCC | CCT | GGT | CGG | CTG | GGC | CGC | TGG | ATC | AGG | ACC | 3145 |
| Ala | Pro | Thr | Gln | Arg | Pro | Pro | Gly | Arg | Leu | Gly | Arg | Trp | Ile | Arg | Thr | |
| 1135 | | | | | 1140 | | | | | 1145 | | | | | 1150 | |
| GTC | TCT | GAT | GAG | GAC | CTT | GAG | TGAGGCTCCT | | GGGAGTCTCC | | CGACACCACC | | | | | 3196 |
| Val | Ser | Asp | Glu | Asp | Leu | Glu | | | | | | | | | | |
| | | | | 1155 | | | | | | | | | | | | |

CGCGCAGGTG TGGACACCAA TTCGGCCTTA CAACATCCCA AATTGGATCC GTTCGCGGGT          3256

CCCCT          3261

( 2 ) INFORMATION FOR SEQ ID NO:30:

( i ) SEQUENCE CHARACTERISTICS:
           ( A ) LENGTH: 1012 amino acids
           ( B ) TYPE: amino acid
           ( D ) TOPOLOGY: linear ( i i ) MOLECULE TYPE: protein ( x i ) SEQUENCE DESCRIPTION: SEQ ID NO:30:

| | | | | | | | | | | | | | | | |
|---|---|---|---|---|---|---|---|---|---|---|---|---|---|---|---|
| Met | Thr | Asn | Leu | Gln | Asp | Gln | Thr | Gln | Gln | Ile | Val | Pro | Phe | Ile | Arg |
| 1 | | | | 5 | | | | | 10 | | | | | 15 | |

-continued

| | | | | | | | | | | | | | | |
|---|---|---|---|---|---|---|---|---|---|---|---|---|---|---|
|Ser|Leu|Leu|Met|Pro|Thr|Thr|Gly|Pro|Ala|Ser|Ile|Pro|Asp|Thr|
| | | |20| | | |25| | | |30| | | |
|Leu|Glu|Lys|His|Thr|Leu|Arg|Ser|Glu|Thr|Ser|Thr|Tyr|Asn|Leu|Thr|
| | | |35| | | |40| | | |45| | | |
|Val|Gly|Asp|Thr|Gly|Ser|Gly|Leu|Ile|Val|Phe|Phe|Pro|Gly|Phe|Pro|
| | | |50| | | |55| | | |60| | | |
|Gly|Ser|Ile|Val|Gly|Ala|His|Tyr|Thr|Leu|Gln|Gly|Asn|Gly|Asn|Tyr|
|65| | | | | |70| | | |75| | | |80|
|Lys|Phe|Asp|Gln|Met|Leu|Leu|Thr|Ala|Gln|Asn|Leu|Pro|Ala|Ser|Tyr|
| | | | |85| | | |90| | | | |95| |
|Asn|Tyr|Cys|Arg|Leu|Val|Ser|Arg|Ser|Leu|Thr|Val|Arg|Ser|Ser|Thr|
| | | |100| | | |105| | | |110| | | |
|Leu|Pro|Gly|Gly|Val|Tyr|Ala|Leu|Asn|Gly|Thr|Ile|Asn|Ala|Val|Thr|
| | | |115| | | |120| | | |125| | | |
|Phe|Gln|Gly|Ser|Leu|Ser|Glu|Leu|Thr|Asp|Val|Ser|Tyr|Asn|Gly|Leu|
| | |130| | | |135| | | |140| | | | |
|Met|Ser|Ala|Thr|Ala|Asn|Ile|Asn|Asp|Lys|Ile|Gly|Asn|Val|Leu|Val|
|145| | | | |150| | | |155| | | | |160|
|Gly|Glu|Gly|Val|Thr|Val|Leu|Ser|Leu|Pro|Thr|Ser|Tyr|Asp|Leu|Gly|
| | | | |165| | | |170| | | |175| | |
|Tyr|Val|Arg|Leu|Gly|Asp|Pro|Ile|Pro|Ala|Ile|Gly|Leu|Asp|Pro|Lys|
| | |180| | | |185| | | |190| | | | |
|Met|Val|Ala|Thr|Cys|Asp|Ser|Ser|Asp|Arg|Pro|Arg|Val|Tyr|Thr|Ile|
| | |195| | | |200| | | |205| | | | |
|Thr|Ala|Ala|Asp|Asp|Tyr|Gln|Phe|Ser|Ser|Gln|Tyr|Gln|Pro|Gly|Gly|
|210| | | | |215| | | |220| | | | | |
|Val|Thr|Ile|Thr|Leu|Phe|Ser|Ala|Asn|Ile|Asp|Ala|Ile|Thr|Ser|Leu|
|225| | | |230| | | |235| | | | | |240|
|Ser|Val|Gly|Gly|Glu|Leu|Val|Phe|Gln|Thr|Ser|Val|His|Gly|Leu|Val|
| | | |245| | | |250| | | |255| | | |
|Leu|Gly|Ala|Thr|Ile|Tyr|Leu|Ile|Gly|Phe|Asp|Gly|Thr|Thr|Val|Ile|
| | |260| | | |265| | | |270| | | | |
|Thr|Arg|Ala|Val|Ala|Ala|Asn|Asn|Gly|Leu|Thr|Thr|Gly|Thr|Asp|Asn|
| |275| | | |280| | | |285| | | | | |
|Leu|Met|Pro|Phe|Asn|Leu|Val|Ile|Pro|Thr|Asn|Glu|Ile|Thr|Gln|Pro|
|290| | | |295| | | |300| | | | | | |
|Ile|Thr|Ser|Ile|Lys|Leu|Glu|Ile|Val|Thr|Ser|Lys|Ser|Gly|Gly|Gln|
|305| | | |310| | | |315| | | | | |320|
|Ala|Gly|Asp|Gln|Met|Ser|Trp|Ser|Ala|Arg|Gly|Ser|Leu|Ala|Val|Thr|
| | | |325| | | |330| | | | |335| | |
|Ile|His|Gly|Gly|Asn|Tyr|Pro|Gly|Ala|Leu|Arg|Pro|Val|Thr|Leu|Val|
| | |340| | | |345| | | |350| | | | |
|Ala|Tyr|Glu|Arg|Val|Ala|Thr|Gly|Ser|Val|Val|Thr|Val|Ala|Gly|Val|
| |355| | | |360| | | |365| | | | | |
|Ser|Asn|Phe|Glu|Leu|Ile|Pro|Asn|Pro|Glu|Leu|Ala|Lys|Asn|Leu|Val|
|370| | | |375| | | |380| | | | | | |
|Thr|Glu|Tyr|Gly|Arg|Phe|Asp|Pro|Gly|Ala|Met|Asn|Tyr|Thr|Lys|Leu|
|385| | | |390| | | |395| | | | | |400|
|Ile|Leu|Ser|Glu|Arg|Asp|Arg|Leu|Gly|Ile|Lys|Thr|Val|Trp|Pro|Thr|
| | | |405| | | |410| | | | |415| | |
|Arg|Glu|Tyr|Thr|Asp|Phe|Arg|Glu|Tyr|Phe|Met|Glu|Val|Ala|Asp|Leu|
| | |420| | | |425| | | |430| | | | |
|Asn|Ser|Pro|Leu|Lys|Ile|Ala|Gly|Ala|Phe|Gly|Phe|Lys|Asp|Ile|Ile|
| |435| | | |440| | | |445| | | | | |

Arg Ala Ile Arg Arg Ile Ala Val Pro Val Val Ser Thr Leu Phe Pro
450                 455                 460

Pro Ala Ala Pro Leu Ala His Ala Ile Gly Glu Gly Val Asp Tyr Leu
465             470              475                 480

Leu Gly Asp Glu Ala Gln Ala Ala Ser Gly Thr Ala Arg Ala Ala Ser
            485              490                 495

Gly Lys Ala Arg Ala Ala Ser Gly Arg Ile Arg Gln Leu Thr Leu Ala
        500              505             510

Ala Asp Lys Gly Tyr Glu Val Val Ala Asn Leu Phe Gln Val Pro Gln
        515             520             525

Asn Pro Val Val Asp Gly Ile Leu Ala Ser Pro Gly Val Leu Arg Gly
    530             535             540

Ala His Asn Leu Asp Cys Val Leu Arg Glu Gly Ala Thr Leu Phe Pro
545             550             555                 560

Val Val Ile Thr Thr Val Glu Asp Ala Met Thr Pro Lys Ala Leu Asn
            565             570             575

Ser Lys Met Phe Ala Val Ile Glu Gly Val Arg Glu Asp Leu Gln Pro
        580             585             590

Pro Ser Gln Arg Gly Ser Phe Ile Arg Thr Leu Ser Gly His Arg Val
        595             600             605

Tyr Gly Tyr Ala Pro Asp Gly Val Leu Pro Leu Glu Thr Gly Arg Asp
    610             615             620

Tyr Thr Val Val Pro Ile Asp Asp Val Trp Asp Ser Ile Met Leu
625             630             635             640

Ser Lys Asp Pro Ile Pro Pro Ile Val Gly Asn Ser Gly Asn Leu Ala
            645             650             655

Ile Ala Tyr Met Asp Val Phe Arg Pro Lys Val Pro Ile His Val Ala
        660             665             670

Met Thr Gly Ala Leu Asn Ala Cys Gly Glu Ile Glu Lys Val Ser Phe
        675             680             685

Arg Ser Thr Lys Leu Ala Thr Ala His Arg Leu Gly Leu Arg Leu Ala
690             695             700

Gly Pro Gly Ala Phe Asp Val Asn Thr Gly Pro Asn Trp Ala Thr Phe
705             710             715             720

Ile Lys Arg Phe Pro His Asn Pro Arg Asp Trp Asp Arg Leu Pro Tyr
            725             730             735

Leu Asn Leu Pro Tyr Leu Pro Pro Asn Ala Gly Arg Gln Tyr His Leu
        740             745             750

Ala Met Ala Ala Ser Glu Phe Lys Glu Thr Pro Glu Leu Glu Ser Ala
        755             760             765

Val Arg Ala Met Glu Ala Ala Ala Asn Val Asp Pro Leu Phe Gln Ser
770             775             780

Ala Leu Ser Val Phe Met Trp Leu Glu Glu Asn Gly Ile Val Thr Asp
785             790             795             800

Met Ala Asn Phe Ala Leu Ser Asp Pro Asn Ala His Arg Met Arg Asn
            805             810             815

Phe Leu Ala Asn Ala Pro Gln Ala Gly Ser Lys Ser Gln Arg Ala Lys
            820             825             830

Tyr Gly Thr Ala Gly Tyr Gly Val Glu Ala Arg Gly Pro Thr Pro Glu
        835             840             845

Glu Ala Gln Arg Glu Lys Asp Thr Arg Ile Ser Lys Lys Met Glu Thr
    850             855             860

Met Gly Ile Tyr Phe Ala Thr Pro Glu Trp Val Ala Leu Asn Gly His

```
865                     870                     875                     880

Arg  Gly  Pro  Ser  Pro  Gly  Gln  Leu  Lys  Tyr  Trp  Gln  Asn  Thr  Arg  Glu
                    885                     890                     895

Ile  Pro  Asp  Pro  Asn  Glu  Asp  Tyr  Leu  Asp  Tyr  Val  His  Ala  Glu  Lys
               900                     905                          910

Ser  Arg  Leu  Ala  Ser  Glu  Glu  Gln  Ile  Leu  Arg  Ala  Ala  Thr  Ser  Ile
          915                          920                    925

Tyr  Gly  Ala  Pro  Gly  Gln  Ala  Glu  Pro  Pro  Gln  Ala  Phe  Ile  Asp  Glu
     930                         935                    940

Val  Ala  Lys  Val  Tyr  Glu  Ile  Asn  His  Gly  Arg  Gly  Pro  Asn  Gln  Glu
945                      950                    955                         960

Gln  Met  Lys  Asp  Leu  Leu  Leu  Thr  Ala  Met  Glu  Met  Lys  His  Arg  Asn
               965                    970                    975

Pro  Arg  Arg  Ala  Leu  Pro  Lys  Pro  Lys  Pro  Lys  Pro  Asn  Ala  Pro  Thr
                980                    985                          990

Gln  Arg  Pro  Pro  Gly  Arg  Leu  Gly  Arg  Trp  Ile  Arg  Thr  Val  Ser  Asp
          995                     1000                   1005

Glu  Asp  Leu  Glu
     1010
```

( 2 ) INFORMATION FOR SEQ ID NO:31:

( i ) SEQUENCE CHARACTERISTICS:
  ( A ) LENGTH: 3264 base pairs
  ( B ) TYPE: nucleic acid
  ( C ) STRANDEDNESS: single
  ( D ) TOPOLOGY: circular ( i i ) MOLECULE TYPE: cDNA ( i x ) FEATURE:
  ( A ) NAME/KEY: CDS
  ( B ) LOCATION: 97..531

( x i ) SEQUENCE DESCRIPTION: SEQ ID NO:31:

```
GGATACGATC  GGTCTGACCC  CGGGGGAGTC  ACCCGGGGAC  AGGCCATCAC  TGCCTTGTTC             60

CTGGTTGGAA  CTCCTCTTTC  TGCTGTACTA  TCGTTG ATG GTG AGT AGA GAT CAG                 114
                                           Met Val Ser Arg Asp Gln
                                                         1015

ACA AAC GAT CGC AGC GAT GAC AAA CCT GAT GGA TCA CAC CCA ACA GAT                    162
Thr Asn Asp Arg Ser Asp Asp Lys Pro Asp Gly Ser His Pro Thr Asp
1020                    1025                    1030

TGT TCC GTT CAT ACG GAG CCT TCT GAT GCC AAC GAC CGG ACC GGC GTC                    210
Cys Ser Val His Thr Glu Pro Ser Asp Ala Asn Asp Arg Thr Gly Val
1035                    1040                    1045                1050

CAT TCC GGA CGA CAC CCT GGA GAA GCA CAC ACT CAG GTC CGA AAC CTC                    258
His Ser Gly Arg His Pro Gly Glu Ala His Thr Gln Val Arg Asn Leu
          1055                    1060                    1065

GAC TTA CAA CTT GAC TGT AGG GGA TAC AGG GTC AGG ACT AAT TGT CTT                    306
Asp Leu Gln Leu Asp Cys Arg Gly Tyr Arg Val Arg Thr Asn Cys Leu
               1070                    1075                    1080

TTT CCC TGG ATT CCC TGG TTC AGT TGT AGG TGC TCA CTA CAC ACT GCA                    354
Phe Pro Trp Ile Pro Trp Phe Ser Cys Arg Cys Ser Leu His Thr Ala
               1085                    1090                    1095

GAG CAG TGG GAA CTA CCA ATT CGA CCA GAT GCT CCT GAC AGC GCA GAA                    402
Glu Gln Trp Glu Leu Pro Ile Arg Pro Asp Ala Pro Asp Ser Ala Glu
          1100                    1105                    1110

CCT GCC TGC CAG CTA CAA CTA CTG CAG GCT AGT GAG CAG GAG TCT AAC                    450
Pro Ala Cys Gln Leu Gln Leu Leu Gln Ala Ser Glu Gln Glu Ser Asn
1115                    1120                    1125                1130
```

```
CGT ACG GTC AAG CAC ACT CCC TGG TGG CGT TTA TGC ACT AAA CGG AAC       498
Arg Thr Val Lys His Thr Pro Trp Trp Arg Leu Cys Thr Lys Arg Asn
                1135                1140              1145

CAT AAA CGC AGT GAC CTT CCA CGG AAG CCT GAG TGAGTTGACT GACTACAGCT     551
His Lys Arg Ser Asp Leu Pro Arg Lys Pro Glu
                1150                1155

ACAACGGGCT GATGTCAGCC ACTGCAACA  TCAACGACAA GATCGGGAAC GTTCTAGTTG     611
GAGAAGGGGT GACTGTTCTC AGTCTACCGA CTTCATATGA CCTTAGTTAT GTGAGACTCG     671
GTGACCCCAT CCCCGCAGCA GGACTCGACC CGAAGTTGAT GGCCACGTGC GACAGTAGTG     731
ACAGACCCAG AGTCTACACC ATAACAGCTG CAGATGAATA CCAATTCTCG TCACAACTCA     791
TCCCGAGTGG CGTGAAGACC ACACTGTTCT CCGCCAACAT CGATGCTCTC ACCAGCTTCA     851
GCGTTGGTGG TGAGCTTGTC TTCAGCCAAG TAACGATCCA AAGCATTGAA GTGGACGTCA     911
CCATTCACTT CATTGGGTTT GACGGGACAG ACGTAGCAGT CAAGGCAGTT GCAACAGACT     971
TTGGGCTGAC AACTGGGACA ACAACCTTG  TGCCATTCAA CCTGGTGGTC CCAACAAATG    1031
AGATCACCCA GCCCATCACT TCCATGAAAC TAGAGGTTGT GACCTACAAG ATTGGCGGCA    1091
CCGCTGGTGA CCCAATATCA TGGACAGTGA GTGGTACACT AGCTGTGACG GTGCACGGAG    1151
GCAACTACCC TGGGCTCTC  CGTCCTGTCA CCCTGGTGGC CTATGAACGA GTGGCTGCAG    1211
GATCTGTTGT CACAGTTGCA GGGGTGAGCA ACTTCGAGCT AATCCCCAAC CCTGAGCTTG    1271
CAAAGAACCT AGTTACAGAG TATGGCCGCT TTGACCCCGG AGCAATGAAC TACACCAAAC    1331
TAATACTGAG TGAGAGAGAT CGTCTAGGCA TCAAGACAGT CTGGCCCACC AGGGAGTACA    1391
CCGATTTCAG GGAGTACTTC ATGGAGGTTG CAGATCTCAA CTCACCCCTA AAGATTGCAG    1451
GAGCATTTGG CTTTAAGGAC ATAATCCGAG CCATTCGGAA GATTGCGGTG CCAGTGGTAT    1511
CCACACTCTT CCCTCCAGCT GCACCCCTAG CACATGCAAT CGGAGAAGGT GTAGACTACC    1571
TCCTGGGCGA CGAGGCCCAA GCAGCCTCAG GACAGCTCG  AGCCGCGTCA GGAAAAGCTA    1631
GAGCTGCCTC AGGACGAATA AGGCAGCTAA CTCTCGCAGC TGACAAGGGG TGCGAGGTAG    1691
TCGCCAACAT GTTCCAGGTG CCCCAGAATC CCATTGTTGA TGGCATTCTG GCATCCCAG    1751
GAATCCTGCG TGGCGCACAC AACCTCGACT GCGTGCTATG GGAGGGAGCC ACTCTTTTCC    1811
CTGTTGTCAT TACGACACTC GAGGATGAGC TGACCCCCAA GGCACTGAAC AGCAAAATGT    1871
TTGCTGTCAT TGAAGGTGTG CGAGAGGACC TCCAGCCTCC ATCCCAACGG GGATCCTTCA    1931
TTCGAACTCT CTCTGGCCAT AGAGTCTATG GCTATGCCCC AGACGGAGTA CTGCCTCTGG    1991
AGACCGGGAG AGACTACACC GTTGTCCCAA TTGATGATGT GTGGGACGAT AGCATAATGC    2051
TGTCGCAGGA CCCCATACCT CCAATCATAG GAACAGCGG  CAACCTAGCC ATAGCATACA    2111
TGGATGTCTT CAGGCCCAAG GTCCCCATCC ACGTGGCTAT GACAGGGGCC CTCAATGCCC    2171
GCGGTGAGAT CGAGAGTGTT ACGTTCCGCA GCACCAAACT CGCCACAGCC CACCGACTTG    2231
GCATGAAGTT AGCTGGTCCT GGAGCCTATG ACATTAATAC AGGACCTAAC TGGGCAACGT    2291
TCGTCAAACG TTTCCCTCAC AATCCCCGAG ACTGGGACAG GTTGCCCTAC CTCAACCTTC    2351
CTTATCTCCC ACCAACAGCA GGACGTCAGT TCCATCTAGC CCTGGCTGCC TCCGAGTTCA    2411
AAGAGACCCC AGAACTCGAA GACGCTGTGC GCGCAATGGA TGCCGCTGCA AATGCCGACC    2471
CATTGTTCCG CTCAGCTCTC CAGGTCTTCA TGTGGTTGGA AGAAACGGG  ATTGTGACCG    2531
ACATGGCTAA CTTCGCCCTC AGCGACCCAA ACGCGCATAG GATGAAAAAC TTCCTAGCAA    2591
ACGCACCCCA GGCTGGAAGC AAGTCGCAGA GGGCCAAGTA TGGCACGGCA GGCTACGGAG    2651
TGGAGGCTCG AGGCCCCACA CCAGAAGAGG CACAGAGGGA AAAAGACACA CGGATCTCCA    2711
```

| | | | | | |
|---|---|---|---|---|---|
| AGAAGATGGA | AACAATGGGC | ATCTACTTCG | CGACACCGGA | ATGGGTGGCT | CTCAACGGGC | 2771
| ACCGAGGCCC | AAGCCCCGGC | CAACTCAAGT | ACTGGCAAAA | CACAAGAGAA | ATACCAGAGC | 2831
| CCAATGAGGA | CTACCCAGAC | TATGTGCACG | CGGAGAAGAG | CCGGTTGGCG | TCAGAAGAAC | 2891
| AGATCCTACG | GGCAGCCACG | TCGATCTACG | GGGCTCCAGG | ACAGGCTGAA | CCACCCCAGG | 2951
| CCTTCATAGA | CGAGGTCGCC | AGGGTCTATG | AAATCAACCA | TGGGCGTGGT | CCAAACCAGG | 3011
| AGCAGATGAA | GGACCTGCTC | CTGACTGCGA | TGGAGATGAA | GCATCGCAAT | CCCAGGCGGG | 3071
| CTCCACCAAA | GCCAAAGCCA | AAACCCAATG | CTCCATCACA | GAGACCCCCT | GGACGGCTGG | 3131
| GCCGCTGGAT | CAGGACGGTC | TCCGACGAGG | ACTTGGAGTG | AGGCTCCTGG | GAGTCTCCCG | 3191
| ACACTACCCG | CGCAGGTGTG | GACACCAATT | CGGCCTTCTA | CCATCCCAAA | TTGGATCCGT | 3251
| TCGCGGGTCC | CCT | | | | | 3264

(2) INFORMATION FOR SEQ ID NO:32:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:32:

```
Met  Val  Ser  Arg  Asp  Gln  Thr  Asn  Asp  Arg  Ser  Asp  Asp  Lys  Pro  Asp
 1              5                  10                      15
Gly  Ser  His  Pro  Thr  Asp  Cys  Ser  Val  His  Thr  Glu  Pro  Ser  Asp  Ala
           20                      25                      30
Asn  Asp  Arg  Thr  Gly  Val  His  Ser  Gly  Arg  His  Pro  Gly  Glu  Ala  His
           35                      40                      45
Thr  Gln  Val  Arg  Asn  Leu  Asp  Leu  Gln  Leu  Asp  Cys  Arg  Gly  Tyr  Arg
     50                      55                      60
Val  Arg  Thr  Asn  Cys  Leu  Phe  Pro  Trp  Ile  Pro  Trp  Phe  Ser  Cys  Arg
 65                      70                      75                      80
Cys  Ser  Leu  His  Thr  Ala  Glu  Gln  Trp  Glu  Leu  Pro  Ile  Arg  Pro  Asp
               85                      90                      95
Ala  Pro  Asp  Ser  Ala  Glu  Pro  Ala  Cys  Gln  Leu  Gln  Leu  Leu  Gln  Ala
              100                     105                     110
Ser  Glu  Gln  Glu  Ser  Asn  Arg  Thr  Val  Lys  His  Thr  Pro  Trp  Trp  Arg
              115                     120                     125
Leu  Cys  Thr  Lys  Arg  Asn  His  Lys  Arg  Ser  Asp  Leu  Pro  Arg  Lys  Pro
              130                     135                     140
Glu
145
```

(2) INFORMATION FOR SEQ ID NO:33:

(i) SEQUENCE CHARACTERISTICS:
        (A) LENGTH: 3264 base pairs
        (B) TYPE: nucleic acid
        (C) STRANDEDNESS: single
        (D) TOPOLOGY: circular (ii) MOLECULE TYPE: cDNA (ix) FEATURE:
        (A) NAME/KEY: CDS
        (B) LOCATION: 131..3169

(xi) SEQUENCE DESCRIPTION: SEQ ID NO:33:

```
GGATACGATC GGTCTGACCC CGGGGGAGTC ACCCGGGGAC AGGCCATCAC TGCCTTGTTC      60

CTGGTTGGAA CTCCTCTTTC TGCTGTACTA TCGTTGATGG TGAGTAGAGA TCAGACAAAC     120

GATCGCAGCG ATG ACA AAC CTG ATG GAT CAC ACC CAA CAG ATT GTT CCG       169
           Met Thr Asn Leu Met Asp His Thr Gln Gln Ile Val Pro
                                150                 155

TTC ATA CGG AGC CTT CTG ATG CCA ACG ACC GGA CCG GCG TCC ATT CCG      217
Phe Ile Arg Ser Leu Leu Met Pro Thr Thr Gly Pro Ala Ser Ile Pro
160                 165                 170

GAC GAC ACC CTG GAG AAG CAC ACA CTC AGG TCC GAA ACC TCG ACT TAC      265
Asp Asp Thr Leu Glu Lys His Thr Leu Arg Ser Glu Thr Ser Thr Tyr
175             180                 185                 190

AAC TTG ACT GTA GGG GAT ACA GGG TCA GGA CTA ATT GTC TTT TTC CCT      313
Asn Leu Thr Val Gly Asp Thr Gly Ser Gly Leu Ile Val Phe Phe Pro
                195                 200                 205

GGA TTC CCT GGT TCA GTT GTA GGT GCT CAC TAC ACA CTG CAG AGC AGT      361
Gly Phe Pro Gly Ser Val Val Gly Ala His Tyr Thr Leu Gln Ser Ser
            210                 215                 220

GGG AAC TAC CAA TTC GAC CAG ATG CTC CTG ACA GCG CAG AAC CTG CCT      409
Gly Asn Tyr Gln Phe Asp Gln Met Leu Leu Thr Ala Gln Asn Leu Pro
        225                 230                 235

GCC AGC TAC AAC TAC TGC AGG CTA GTG AGC AGG AGT CTA ACC GTA CGG      457
Ala Ser Tyr Asn Tyr Cys Arg Leu Val Ser Arg Ser Leu Thr Val Arg
240                 245                 250

TCA AGC ACA CTC CCT GGT GGC GTT TAT GCA CTA AAC GGA ACC ATA AAC      505
Ser Ser Thr Leu Pro Gly Gly Val Tyr Ala Leu Asn Gly Thr Ile Asn
255                 260                 265                 270

GCA GTG ACC TTC CAC GGA AGC CTG AGT GAG TTG ACT GAC TAC AGC TAC      553
Ala Val Thr Phe His Gly Ser Leu Ser Glu Leu Thr Asp Tyr Ser Tyr
                275                 280                 285

AAC GGG CTG ATG TCA GCC ACT GCG AAC ATC AAC GAC AAG ATC GGG AAC      601
Asn Gly Leu Met Ser Ala Thr Ala Asn Ile Asn Asp Lys Ile Gly Asn
            290                 295                 300

GTT CTA GTT GGA GAA GGG GTG ACT GTT CTC AGT CTA CCG ACT TCA TAT      649
Val Leu Val Gly Glu Gly Val Thr Val Leu Ser Leu Pro Thr Ser Tyr
        305                 310                 315

GAC CTT AGT TAT GTG AGA CTC GGT GAC CCC ATC CCC GCA GCA GGA CTC      697
Asp Leu Ser Tyr Val Arg Leu Gly Asp Pro Ile Pro Ala Ala Gly Leu
320                 325                 330

GAC CCG AAG TTG ATG GCC ACG TGC GAC AGT AGT GAC AGA CCC AGA GTC      745
Asp Pro Lys Leu Met Ala Thr Cys Asp Ser Ser Asp Arg Pro Arg Val
335                 340                 345                 350

TAC ACC ATA ACA GCT GCA GAT GAA TAC CAA TTC TCG TCA CAA CTC ATC      793
Tyr Thr Ile Thr Ala Ala Asp Glu Tyr Gln Phe Ser Ser Gln Leu Ile
                355                 360                 365

CCG AGT GGC GTG AAG ACC ACA CTG TTC TCC GCC AAC ATC GAT GCT CTC      841
Pro Ser Gly Val Lys Thr Thr Leu Phe Ser Ala Asn Ile Asp Ala Leu
            370                 375                 380

ACC AGC TTC AGC GTT GGT GGT GAG CTT GTC TTC AGC CAA GTA ACG ATC      889
Thr Ser Phe Ser Val Gly Gly Glu Leu Val Phe Ser Gln Val Thr Ile
        385                 390                 395

CAA AGC ATT GAA GTG GAC GTC ACC ATT CAC TTC ATT GGG TTT GAC GGG      937
Gln Ser Ile Glu Val Asp Val Thr Ile His Phe Ile Gly Phe Asp Gly
400                 405                 410

ACA GAC GTA GCA GTC AAG GCA GTT GCA ACA GAC TTT GGG CTG ACA ACT      985
Thr Asp Val Ala Val Lys Ala Val Ala Thr Asp Phe Gly Leu Thr Thr
415                 420                 425                 430

GGG ACA AAC AAC CTT GTG CCA TTC AAC CTG GTG GTC CCA ACA AAT GAG     1033
Gly Thr Asn Asn Leu Val Pro Phe Asn Leu Val Val Pro Thr Asn Glu
                435                 440                 445
```

```
ATC ACC CAG CCC ATC ACT TCC ATG AAA CTA GAG GTT GTG ACC TAC AAG      1081
Ile Thr Gln Pro Ile Thr Ser Met Lys Leu Glu Val Val Thr Tyr Lys
            450             455                 460

ATT GGC GGC ACC GCT GGT GAC CCA ATA TCA TGG ACA GTG AGT GGT ACA      1129
Ile Gly Gly Thr Ala Gly Asp Pro Ile Ser Trp Thr Val Ser Gly Thr
            465             470                 475

CTA GCT GTG ACG GTG CAC GGA GGC AAC TAC CCT GGG GCT CTC CGT CCT      1177
Leu Ala Val Thr Val His Gly Gly Asn Tyr Pro Gly Ala Leu Arg Pro
        480             485                 490

GTC ACC CTG GTG GCC TAT GAA CGA GTG GCT GCA GGA TCT GTT GTC ACA      1225
Val Thr Leu Val Ala Tyr Glu Arg Val Ala Ala Gly Ser Val Val Thr
495             500             505                 510

GTT GCA GGG GTG AGC AAC TTC GAG CTA ATC CCC AAC CCT GAG CTT GCA      1273
Val Ala Gly Val Ser Asn Phe Glu Leu Ile Pro Asn Pro Glu Leu Ala
                515             520                 525

AAG AAC CTA GTT ACA GAG TAT GGC CGC TTT GAC CCC GGA GCA ATG AAC      1321
Lys Asn Leu Val Thr Glu Tyr Gly Arg Phe Asp Pro Gly Ala Met Asn
            530             535                 540

TAC ACC AAA CTA ATA CTG AGT GAG AGA GAT CGT CTA GGC ATC AAG ACA      1369
Tyr Thr Lys Leu Ile Leu Ser Glu Arg Asp Arg Leu Gly Ile Lys Thr
            545             550                 555

GTC TGG CCC ACC AGG GAG TAC ACC GAT TTC AGG GAG TAC TTC ATG GAG      1417
Val Trp Pro Thr Arg Glu Tyr Thr Asp Phe Arg Glu Tyr Phe Met Glu
    560             565                 570

GTT GCA GAT CTC AAC TCA CCC CTA AAG ATT GCA GGA GCA TTT GGC TTT      1465
Val Ala Asp Leu Asn Ser Pro Leu Lys Ile Ala Gly Ala Phe Gly Phe
575             580             585                 590

AAG GAC ATA ATC CGA GCC ATT CGG AAG ATT GCG GTG CCA GTG GTA TCC      1513
Lys Asp Ile Ile Arg Ala Ile Arg Lys Ile Ala Val Pro Val Val Ser
                595             600                 605

ACA CTC TTC CCT CCA GCT GCA CCC CTA GCA CAT GCA ATC GGA GAA GGT      1561
Thr Leu Phe Pro Pro Ala Ala Pro Leu Ala His Ala Ile Gly Glu Gly
            610             615                 620

GTA GAC TAC CTC CTG GGC GAC GAG GCC CAA GCA GCC TCA GGG ACA GCT      1609
Val Asp Tyr Leu Leu Gly Asp Glu Ala Gln Ala Ala Ser Gly Thr Ala
            625             630                 635

CGA GCC GCG TCA GGA AAA GCT AGA GCT GCC TCA GGA CGA ATA AGG CAG      1657
Arg Ala Ala Ser Gly Lys Ala Arg Ala Ala Ser Gly Arg Ile Arg Gln
            640             645                 650

CTA ACT CTC GCA GCT GAC AAG GGG TGC GAG GTA GTC GCC AAC ATG TTC      1705
Leu Thr Leu Ala Ala Asp Lys Gly Cys Glu Val Val Ala Asn Met Phe
655             660                 665                 670

CAG GTG CCC CAG AAT CCC ATT GTT GAT GGC ATT CTG GCA TCC CCA GGA      1753
Gln Val Pro Gln Asn Pro Ile Val Asp Gly Ile Leu Ala Ser Pro Gly
            675             680                 685

ATC CTG CGT GGC GCA CAC AAC CTC GAC TGC GTG CTA TGG GAG GGA GCC      1801
Ile Leu Arg Gly Ala His Asn Leu Asp Cys Val Leu Trp Glu Gly Ala
            690             695                 700

ACT CTT TTC CCT GTT GTC ATT ACG ACA CTC GAG GAT GAG CTG ACC CCC      1849
Thr Leu Phe Pro Val Val Ile Thr Thr Leu Glu Asp Glu Leu Thr Pro
        705             710                 715

AAG GCA CTG AAC AGC AAA ATG TTT GCT GTC ATT GAA GGT GTG CGA GAG      1897
Lys Ala Leu Asn Ser Lys Met Phe Ala Val Ile Glu Gly Val Arg Glu
    720             725                 730

GAC CTC CAG CCT CCA TCC CAA CGG GGA TCC TTC ATT CGA ACT CTC TCT      1945
Asp Leu Gln Pro Pro Ser Gln Arg Gly Ser Phe Ile Arg Thr Leu Ser
735             740                 745                 750

GGC CAT AGA GTC TAT GGC TAT GCC CCA GAC GGA GTA CTG CCT CTG GAG      1993
Gly His Arg Val Tyr Gly Tyr Ala Pro Asp Gly Val Leu Pro Leu Glu
            755             760                 765
```

| | | | | | | | | | | | | | | | | |
|---|---|---|---|---|---|---|---|---|---|---|---|---|---|---|---|---|
| ACC | GGG | AGA | GAC | TAC | ACC | GTT | GTC | CCA | ATT | GAT | GAT | GTG | TGG | GAC | GAT | 2041 |
| Thr | Gly | Arg | Asp | Tyr | Thr | Val | Val | Pro | Ile | Asp | Asp | Val | Trp | Asp | Asp | |
| | | 770 | | | | | 775 | | | | | 780 | | | | |
| AGC | ATA | ATG | CTG | TCG | CAG | GAC | CCC | ATA | CCT | CCA | ATC | ATA | GGG | AAC | AGC | 2089 |
| Ser | Ile | Met | Leu | Ser | Gln | Asp | Pro | Ile | Pro | Pro | Ile | Ile | Gly | Asn | Ser | |
| | 785 | | | | | 790 | | | | | 795 | | | | | |
| GGC | AAC | CTA | GCC | ATA | GCA | TAC | ATG | GAT | GTC | TTC | AGG | CCC | AAG | GTC | CCC | 2137 |
| Gly | Asn | Leu | Ala | Ile | Ala | Tyr | Met | Asp | Val | Phe | Arg | Pro | Lys | Val | Pro | |
| | 800 | | | | 805 | | | | | 810 | | | | | | |
| ATC | CAC | GTG | GCT | ATG | ACA | GGG | GCC | CTC | AAT | GCC | CGC | GGT | GAG | ATC | GAG | 2185 |
| Ile | His | Val | Ala | Met | Thr | Gly | Ala | Leu | Asn | Ala | Arg | Gly | Glu | Ile | Glu | |
| 815 | | | | 820 | | | | | 825 | | | | | 830 | | |
| AGT | GTT | ACG | TTC | CGC | AGC | ACC | AAA | CTC | GCC | ACA | GCC | CAC | CGA | CTT | GGC | 2233 |
| Ser | Val | Thr | Phe | Arg | Ser | Thr | Lys | Leu | Ala | Thr | Ala | His | Arg | Leu | Gly | |
| | | | | 835 | | | | | 840 | | | | | 845 | | |
| ATG | AAG | TTA | GCT | GGT | CCT | GGA | GCC | TAT | GAC | ATT | AAT | ACA | GGA | CCT | AAC | 2281 |
| Met | Lys | Leu | Ala | Gly | Pro | Gly | Ala | Tyr | Asp | Ile | Asn | Thr | Gly | Pro | Asn | |
| | | | 850 | | | | | 855 | | | | | 860 | | | |
| TGG | GCA | ACG | TTC | GTC | AAA | CGT | TTC | CCT | CAC | AAT | CCC | CGA | GAC | TGG | GAC | 2329 |
| Trp | Ala | Thr | Phe | Val | Lys | Arg | Phe | Pro | His | Asn | Pro | Arg | Asp | Trp | Asp | |
| | | 865 | | | | | 870 | | | | | 875 | | | | |
| AGG | TTG | CCC | TAC | CTC | AAC | CTT | CCT | TAT | CTC | CCA | CCA | ACA | GCA | GGA | CGT | 2377 |
| Arg | Leu | Pro | Tyr | Leu | Asn | Leu | Pro | Tyr | Leu | Pro | Pro | Thr | Ala | Gly | Arg | |
| | 880 | | | | | 885 | | | | | 890 | | | | | |
| CAG | TTC | CAT | CTA | GCC | CTG | GCT | GCC | TCC | GAG | TTC | AAA | GAG | ACC | CCA | GAA | 2425 |
| Gln | Phe | His | Leu | Ala | Leu | Ala | Ala | Ser | Glu | Phe | Lys | Glu | Thr | Pro | Glu | |
| 895 | | | | | 900 | | | | | 905 | | | | | 910 | |
| CTC | GAA | GAC | GCT | GTG | CGC | GCA | ATG | GAT | GCC | GCT | GCA | AAT | GCC | GAC | CCA | 2473 |
| Leu | Glu | Asp | Ala | Val | Arg | Ala | Met | Asp | Ala | Ala | Ala | Asn | Ala | Asp | Pro | |
| | | | | 915 | | | | | 920 | | | | | 925 | | |
| TTG | TTC | CGC | TCA | GCT | CTC | CAG | GTC | TTC | ATG | TGG | TTG | GAA | GAA | AAC | GGG | 2521 |
| Leu | Phe | Arg | Ser | Ala | Leu | Gln | Val | Phe | Met | Trp | Leu | Glu | Glu | Asn | Gly | |
| | | | 930 | | | | | 935 | | | | | 940 | | | |
| ATT | GTG | ACC | GAC | ATG | GCT | AAC | TTC | GCC | CTC | AGC | GAC | CCA | AAC | GCG | CAT | 2569 |
| Ile | Val | Thr | Asp | Met | Ala | Asn | Phe | Ala | Leu | Ser | Asp | Pro | Asn | Ala | His | |
| | | 945 | | | | | 950 | | | | | 955 | | | | |
| AGG | ATG | AAA | AAC | TTC | CTA | GCA | AAC | GCA | CCC | CAG | GCT | GGA | AGC | AAG | TCG | 2617 |
| Arg | Met | Lys | Asn | Phe | Leu | Ala | Asn | Ala | Pro | Gln | Ala | Gly | Ser | Lys | Ser | |
| | 960 | | | | | 965 | | | | | 970 | | | | | |
| CAG | AGG | GCC | AAG | TAT | GGC | ACG | GCA | GGC | TAC | GGA | GTG | GAG | GCT | CGA | GGC | 2665 |
| Gln | Arg | Ala | Lys | Tyr | Gly | Thr | Ala | Gly | Tyr | Gly | Val | Glu | Ala | Arg | Gly | |
| 975 | | | | | 980 | | | | | 985 | | | | | 990 | |
| CCC | ACA | CCA | GAA | GAG | GCA | CAG | AGG | GAA | AAA | GAC | ACA | CGG | ATC | TCC | AAG | 2713 |
| Pro | Thr | Pro | Glu | Glu | Ala | Gln | Arg | Glu | Lys | Asp | Thr | Arg | Ile | Ser | Lys | |
| | | | | 995 | | | | | 1000 | | | | | 1005 | | |
| AAG | ATG | GAA | ACA | ATG | GGC | ATC | TAC | TTC | GCG | ACA | CCG | GAA | TGG | GTG | GCT | 2761 |
| Lys | Met | Glu | Thr | Met | Gly | Ile | Tyr | Phe | Ala | Thr | Pro | Glu | Trp | Val | Ala | |
| | | | | 1010 | | | | | 1015 | | | | | 1020 | | |
| CTC | AAC | GGG | CAC | CGA | GGC | CCA | AGC | CCC | GGC | CAA | CTC | AAG | TAC | TGG | CAA | 2809 |
| Leu | Asn | Gly | His | Arg | Gly | Pro | Ser | Pro | Gly | Gln | Leu | Lys | Tyr | Trp | Gln | |
| | | | 1025 | | | | | 1030 | | | | | 1035 | | | |
| AAC | ACA | AGA | GAA | ATA | CCA | GAG | CCC | AAT | GAG | GAC | TAC | CCA | GAC | TAT | GTG | 2857 |
| Asn | Thr | Arg | Glu | Ile | Pro | Glu | Pro | Asn | Glu | Asp | Tyr | Pro | Asp | Tyr | Val | |
| | | 1040 | | | | | 1045 | | | | | 1050 | | | | |
| CAC | GCG | GAG | AAG | AGC | CGG | TTG | GCG | TCA | GAA | GAA | CAG | ATC | CTA | CGG | GCA | 2905 |
| His | Ala | Glu | Lys | Ser | Arg | Leu | Ala | Ser | Glu | Glu | Gln | Ile | Leu | Arg | Ala | |
| 1055 | | | | | 1060 | | | | | 1065 | | | | | 1070 | |
| GCC | ACG | TCG | ATC | TAC | GGG | GCT | CCA | GGA | CAG | GCT | GAA | CCA | CCC | CAG | GCC | 2953 |
| Ala | Thr | Ser | Ile | Tyr | Gly | Ala | Pro | Gly | Gln | Ala | Glu | Pro | Pro | Gln | Ala | |
| | | | | 1075 | | | | | 1080 | | | | | 1085 | | |

| | | | | | | | | | | | | | | | | |
|---|---|---|---|---|---|---|---|---|---|---|---|---|---|---|---|---|
| TTC | ATA | GAC | GAG | GTC | GCC | AGG | GTC | TAT | GAA | ATC | AAC | CAT | GGG | CGT | GGT | 3001 |
| Phe | Ile | Asp | Glu | Val | Ala | Arg | Val | Tyr | Glu | Ile | Asn | His | Gly | Arg | Gly | |
| | | | 1090 | | | | 1095 | | | | | 1100 | | | | |
| CCA | AAC | CAG | GAG | CAG | ATG | AAG | GAC | CTG | CTC | CTG | ACT | GCG | ATG | GAG | ATG | 3049 |
| Pro | Asn | Gln | Glu | Gln | Met | Lys | Asp | Leu | Leu | Leu | Thr | Ala | Met | Glu | Met | |
| | | 1105 | | | | | 1110 | | | | | 1115 | | | | |
| AAG | CAT | CGC | AAT | CCC | AGG | CGG | GCT | CCA | CCA | AAG | CCA | AAG | CCA | AAA | CCC | 3097 |
| Lys | His | Arg | Asn | Pro | Arg | Arg | Ala | Pro | Pro | Lys | Pro | Lys | Pro | Lys | Pro | |
| | | 1120 | | | | 1125 | | | | | 1130 | | | | | |
| AAT | GCT | CCA | TCA | CAG | AGA | CCC | CCT | GGA | CGG | CTG | GGC | CGC | TGG | ATC | AGG | 3145 |
| Asn | Ala | Pro | Ser | Gln | Arg | Pro | Pro | Gly | Arg | Leu | Gly | Arg | Trp | Ile | Arg | |
| 1135 | | | | | 1140 | | | | | 1145 | | | | | 1150 | |
| ACG | GTC | TCC | GAC | GAG | GAC | TTG | GAG | TGAGGCTCCT | GGGAGTCTCC | CGACACTACC | | | | | | 3199 |
| Thr | Val | Ser | Asp | Glu | Asp | Leu | Glu | | | | | | | | | |
| | | | 1155 | | | | | | | | | | | | | |

CGCGCAGGTG TGGACACCAA TTCGGCCTTC TACCATCCCA AATTGGATCC GTTCGCGGGT  3259

CCCCT  3264

( 2 ) INFORMATION FOR SEQ ID NO:34:

( i ) SEQUENCE CHARACTERISTICS:
        ( A ) LENGTH: 1013 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

| | | | | | | | | | | | | | | |
|---|---|---|---|---|---|---|---|---|---|---|---|---|---|---|
| Met | Thr | Asn | Leu | Met | Asp | His | Thr | Gln | Gln | Ile | Val | Pro | Phe | Ile | Arg |
| 1 | | | | 5 | | | | | 10 | | | | | 15 | |
| Ser | Leu | Leu | Met | Pro | Thr | Thr | Gly | Pro | Ala | Ser | Ile | Pro | Asp | Asp | Thr |
| | | | | 20 | | | | | 25 | | | | | 30 | |
| Leu | Glu | Lys | His | Thr | Leu | Arg | Ser | Glu | Thr | Ser | Thr | Tyr | Asn | Leu | Thr |
| | | | | 35 | | | | | 40 | | | | | 45 | |
| Val | Gly | Asp | Thr | Gly | Ser | Gly | Leu | Ile | Val | Phe | Phe | Pro | Gly | Phe | Pro |
| | | | 50 | | | | | 55 | | | | | 60 | | |
| Gly | Ser | Val | Val | Gly | Ala | His | Tyr | Thr | Leu | Gln | Ser | Ser | Gly | Asn | Tyr |
| 65 | | | | | 70 | | | | | 75 | | | | | 80 |
| Gln | Phe | Asp | Gln | Met | Leu | Leu | Thr | Ala | Gln | Asn | Leu | Pro | Ala | Ser | Tyr |
| | | | | 85 | | | | | 90 | | | | | 95 | |
| Asn | Tyr | Cys | Arg | Leu | Val | Ser | Arg | Ser | Leu | Thr | Val | Arg | Ser | Ser | Thr |
| | | | | 100 | | | | | 105 | | | | | 110 | |
| Leu | Pro | Gly | Gly | Val | Tyr | Ala | Leu | Asn | Gly | Thr | Ile | Asn | Ala | Val | Thr |
| | | | | 115 | | | | | 120 | | | | | 125 | |
| Phe | His | Gly | Ser | Leu | Ser | Glu | Leu | Thr | Asp | Tyr | Ser | Tyr | Asn | Gly | Leu |
| | | 130 | | | | | 135 | | | | | 140 | | | |
| Met | Ser | Ala | Thr | Ala | Asn | Ile | Asn | Asp | Lys | Ile | Gly | Asn | Val | Leu | Val |
| 145 | | | | | 150 | | | | | 155 | | | | | 160 |
| Gly | Glu | Gly | Val | Thr | Val | Leu | Ser | Leu | Pro | Thr | Ser | Tyr | Asp | Leu | Ser |
| | | | | 165 | | | | | 170 | | | | | 175 | |
| Tyr | Val | Arg | Leu | Gly | Asp | Pro | Ile | Pro | Ala | Ala | Gly | Leu | Asp | Pro | Lys |
| | | | 180 | | | | | 185 | | | | | 190 | | |
| Leu | Met | Ala | Thr | Cys | Asp | Ser | Ser | Asp | Arg | Pro | Arg | Val | Tyr | Thr | Ile |
| | | | 195 | | | | | 200 | | | | | 205 | | |
| Thr | Ala | Ala | Asp | Glu | Tyr | Gln | Phe | Ser | Ser | Gln | Leu | Ile | Pro | Ser | Gly |
| | | 210 | | | | | 215 | | | | | 220 | | | |
| Val | Lys | Thr | Thr | Leu | Phe | Ser | Ala | Asn | Ile | Asp | Ala | Leu | Thr | Ser | Phe |
| 225 | | | | | 230 | | | | | 235 | | | | | 240 |

Ser Val Gly Gly Glu Leu Val Phe Ser Gln Val Thr Ile Gln Ser Ile
                245                 250                 255

Glu Val Asp Val Thr Ile His Phe Ile Gly Phe Asp Gly Thr Asp Val
            260                 265                 270

Ala Val Lys Ala Val Ala Thr Asp Phe Gly Leu Thr Thr Gly Thr Asn
        275                 280                 285

Asn Leu Val Pro Phe Asn Leu Val Val Pro Thr Asn Glu Ile Thr Gln
    290                 295                 300

Pro Ile Thr Ser Met Lys Leu Glu Val Val Thr Tyr Lys Ile Gly Gly
305                 310                 315                 320

Thr Ala Gly Asp Pro Ile Ser Trp Thr Val Ser Gly Thr Leu Ala Val
                325                 330                 335

Thr Val His Gly Gly Asn Tyr Pro Gly Ala Leu Arg Pro Val Thr Leu
            340                 345                 350

Val Ala Tyr Glu Arg Val Ala Ala Gly Ser Val Val Thr Val Ala Gly
        355                 360                 365

Val Ser Asn Phe Glu Leu Ile Pro Asn Pro Glu Leu Ala Lys Asn Leu
    370                 375                 380

Val Thr Glu Tyr Gly Arg Phe Asp Pro Gly Ala Met Asn Tyr Thr Lys
385                 390                 395                 400

Leu Ile Leu Ser Arg Asp Arg Leu Gly Ile Lys Thr Val Trp Pro
                405                 410                 415

Thr Arg Glu Tyr Thr Asp Phe Arg Glu Tyr Phe Met Glu Val Ala Asp
            420                 425                 430

Leu Asn Ser Pro Leu Lys Ile Ala Gly Ala Phe Gly Phe Lys Asp Ile
        435                 440                 445

Ile Arg Ala Ile Arg Lys Ile Ala Val Pro Val Val Ser Thr Leu Phe
    450                 455                 460

Pro Pro Ala Ala Pro Leu Ala His Ala Ile Gly Glu Gly Val Asp Tyr
465                 470                 475                 480

Leu Leu Gly Asp Glu Ala Gln Ala Ala Ser Gly Thr Ala Arg Ala Ala
                485                 490                 495

Ser Gly Lys Ala Arg Ala Ala Ser Gly Arg Ile Arg Gln Leu Thr Leu
            500                 505                 510

Ala Ala Asp Lys Gly Cys Glu Val Ala Asn Met Phe Gln Val Pro
        515                 520                 525

Gln Asn Pro Ile Val Asp Gly Ile Leu Ala Ser Pro Gly Ile Leu Arg
    530                 535                 540

Gly Ala His Asn Leu Asp Cys Val Leu Trp Glu Gly Ala Thr Leu Phe
545                 550                 555                 560

Pro Val Val Ile Thr Thr Leu Glu Asp Glu Leu Thr Pro Lys Ala Leu
                565                 570                 575

Asn Ser Lys Met Phe Ala Val Ile Glu Gly Val Arg Glu Asp Leu Gln
            580                 585                 590

Pro Pro Ser Gln Arg Gly Ser Phe Ile Arg Thr Leu Ser Gly His Arg
        595                 600                 605

Val Tyr Gly Tyr Ala Pro Asp Gly Val Leu Pro Leu Glu Thr Gly Arg
    610                 615                 620

Asp Tyr Thr Val Val Pro Ile Asp Asp Val Trp Asp Asp Ser Ile Met
625                 630                 635                 640

Leu Ser Gln Asp Pro Ile Pro Pro Ile Ile Gly Asn Ser Gly Asn Leu
                645                 650                 655

Ala Ile Ala Tyr Met Asp Val Phe Arg Pro Lys Val Pro Ile His Val

|   |   |   |   |   | 660 |   |   |   |   | 665 |   |   |   |   | 670 |   |   |
|---|---|---|---|---|---|---|---|---|---|---|---|---|---|---|---|---|---|
| Ala | Met | Thr 675 | Gly | Ala | Leu | Asn | Ala | Arg 680 | Gly | Glu | Ile | Glu 685 | Ser | Val | Thr |
| Phe | Arg 690 | Ser | Thr | Lys | Leu | Ala 695 | Thr | Ala | His | Arg | Leu 700 | Gly | Met | Lys | Leu |
| Ala 705 | Gly | Pro | Gly | Ala | Tyr 710 | Asp | Ile | Asn | Thr | Gly 715 | Pro | Asn | Trp | Ala | Thr 720 |
| Phe | Val | Lys | Arg | Phe 725 | Pro | His | Asn | Pro | Arg 730 | Asp | Trp | Asp | Arg | Leu 735 | Pro |
| Tyr | Leu | Asn | Leu 740 | Pro | Tyr | Leu | Pro | Pro 745 | Thr | Ala | Gly | Arg | Gln 750 | Phe | His |
| Leu | Ala | Leu 755 | Ala | Ala | Ser | Glu | Phe 760 | Lys | Glu | Thr | Pro | Glu 765 | Leu | Glu | Asp |
| Ala | Val | Arg 770 | Ala | Met | Asp | Ala 775 | Ala | Ala | Asn | Ala | Asp 780 | Pro | Leu | Phe | Arg |
| Ser 785 | Ala | Leu | Gln | Val | Phe 790 | Met | Trp | Leu | Glu | Glu 795 | Asn | Gly | Ile | Val | Thr 800 |
| Asp | Met | Ala | Asn | Phe 805 | Ala | Leu | Ser | Asp | Pro 810 | Asn | Ala | His | Arg | Met 815 | Lys |
| Asn | Phe | Leu | Ala 820 | Asn | Ala | Pro | Gln | Ala 825 | Gly | Ser | Lys | Ser | Gln 830 | Arg | Ala |
| Lys | Tyr | Gly 835 | Thr | Ala | Gly | Tyr | Gly 840 | Val | Glu | Ala | Arg | Gly 845 | Pro | Thr | Pro |
| Glu | Glu 850 | Ala | Gln | Arg | Glu | Lys 855 | Asp | Thr | Arg | Ile | Ser 860 | Lys | Lys | Met | Glu |
| Thr 865 | Met | Gly | Ile | Tyr | Phe 870 | Ala | Thr | Pro | Glu | Trp 875 | Val | Ala | Leu | Asn | Gly 880 |
| His | Arg | Gly | Pro | Ser 885 | Pro | Gly | Gln | Leu | Lys 890 | Tyr | Trp | Gln | Asn | Thr 895 | Arg |
| Glu | Ile | Pro | Glu 900 | Pro | Asn | Glu | Asp | Tyr 905 | Pro | Asp | Tyr | Val | His 910 | Ala | Glu |
| Lys | Ser | Arg 915 | Leu | Ala | Ser | Glu | Gln 920 | Ile | Leu | Arg | Ala 925 | Ala | Thr | Ser |
| Ile | Tyr 930 | Gly | Ala | Pro | Gly | Gln 935 | Ala | Glu | Pro | Pro | Gln 940 | Ala | Phe | Ile | Asp |
| Glu 945 | Val | Ala | Arg | Val | Tyr 950 | Glu | Ile | Asn | His | Gly 955 | Arg | Gly | Pro | Asn | Gln 960 |
| Glu | Gln | Met | Lys | Asp 965 | Leu | Leu | Leu | Thr | Ala 970 | Met | Glu | Met | Lys | His 975 | Arg |
| Asn | Pro | Arg | Arg 980 | Ala | Pro | Pro | Lys | Pro 985 | Lys | Pro | Lys | Pro | Asn 990 | Ala | Pro |
| Ser | Gln | Arg 995 | Pro | Pro | Gly | Arg | Leu 1000 | Gly | Arg | Trp | Ile | Arg 1005 | Thr | Val | Ser |
| Asp | Glu | Asp 1010 | Leu | Glu |   |   |   |   |   |   |   |   |   |   |   |